US006987263B2

(12) United States Patent
Hobbs et al.

(10) Patent No.: US 6,987,263 B2
(45) Date of Patent: Jan. 17, 2006

(54) HIGH THROUGHPUT SYSTEMS AND METHODS FOR PARALLEL SAMPLE ANALYSIS

(75) Inventors: Steven E. Hobbs, West Hills, CA (US); Stephen D. O'Connor, Pasadena, CA (US); Ronald C. Gamble, Altadena, CA (US)

(73) Assignee: Nanostream, Inc., Pasadena, CA (US)

( * ) Notice: Subject to any disclaimer, the term of this patent is extended or adjusted under 35 U.S.C. 154(b) by 89 days.

(21) Appl. No.: 10/736,154

(22) Filed: Dec. 13, 2003

(65) Prior Publication Data

US 2004/0217279 A1   Nov. 4, 2004

Related U.S. Application Data

(60) Provisional application No. 60/433,449, filed on Dec. 13, 2002.

(51) Int. Cl.
B01D 54/44 (2006.01)
H01J 49/00 (2006.01)
(52) U.S. Cl. ...................................... 250/288; 250/287
(58) Field of Classification Search ................ 250/288, 250/283, 281, 282, 287
See application file for complete search history.

(56) References Cited

U.S. PATENT DOCUMENTS

| | | | | |
|---|---|---|---|---|
| 4,507,555 | A | | 3/1985 | Chang ......................... 250/281 |
| 4,840,074 | A | | 6/1989 | Jessop ....................... 73/864.81 |
| 5,071,547 | A | | 12/1991 | Cazer et al. ............. 210/198.2 |
| 5,401,963 | A | * | 3/1995 | Sittler ......................... 250/288 |
| 5,872,010 | A | * | 2/1999 | Karger et al. ................ 436/173 |
| 5,917,184 | A | | 6/1999 | Carson et al. ............... 250/288 |
| 6,012,488 | A | | 1/2000 | Nichols ................. 137/625.11 |
| 6,066,848 | A | * | 5/2000 | Kassel et al. ................ 250/288 |
| 6,175,112 | B1 | * | 1/2001 | Karger et al. ................ 250/288 |
| 6,191,418 | B1 | | 2/2001 | Hindsgaul et al. .......... 250/288 |

(Continued)

FOREIGN PATENT DOCUMENTS

EP      EP 1 106 244 A2    6/2001

(Continued)

OTHER PUBLICATIONS

"Multi-Parallel-HPLC," Web document published at: http://www.sepiatec.com/download/phplc.pdf, SEPIAtec GmbH, Louis-Blériot-Strasse 5 D-12487 Berlin Germany.

(Continued)

Primary Examiner—John R. Lee
Assistant Examiner—Kalimah Fernandez
(74) Attorney, Agent, or Firm—Vincent K. Gustafson

(57) ABSTRACT

Systems for analyzing multiple samples in parallel using mass spectrometric preferably coupled with fluid phase separation techniques are provided. A multi-analyzer mass spectrometer includes multiple inlets, multiple mass analyzers, and multiple transducers to conduct mass analyses of multiple samples in parallel. A modular mass analyzer may include a vacuum enclosure, a chassis, and multiple mass analysis modules disposed within the chassis. Modules are preferably disposed in a spatially compact two-dimensional array. A common multi-stage vacuum system may be utilized in conjunction with baffles or partitions disposed within and between modules to maintain differential vacuum conditions within the spectrometer utilizing a minimum number of pumps. Common control inputs may be provided to multiple modules or other components within a multi-analyzer spectrometer. Fluid phase separation devices for use with a multi-analyzer spectrometer may be microfluidic devices utilizing chromatographic, electrophoretic, or other separation methods.

45 Claims, 17 Drawing Sheets

U.S. PATENT DOCUMENTS

| | | | |
|---|---|---|---|
| 6,264,892 B1 * | 7/2001 | Kaltenbach et al. | 422/68.1 |
| 6,296,771 B1 | 10/2001 | Miroslav | 210/656 |
| 6,316,768 B1 | 11/2001 | Rockwood et al. | 250/287 |
| 6,318,157 B1 * | 11/2001 | Corso et al. | 73/61.52 |
| 6,369,893 B1 | 4/2002 | Christel et al. | 356/417 |
| 6,410,915 B1 * | 6/2002 | Bateman et al. | 250/288 |
| 6,437,345 B1 | 8/2002 | Bruno-Raimondi et al. | 250/458.1 |
| 6,464,866 B2 | 10/2002 | Moon et al. | 210/198.2 |
| 6,532,978 B1 | 3/2003 | Müller-Kuhrt et al. | 137/1 |
| 6,547,941 B2 | 4/2003 | Kopf-Sill et al. | 204/452 |
| 6,580,070 B2 * | 6/2003 | Cornish et al. | 250/287 |
| 6,581,441 B1 | 6/2003 | Paul | 73/61.52 |
| 6,586,727 B2 * | 7/2003 | Bateman et al. | 250/282 |
| 6,613,581 B1 | 9/2003 | Wada et al. | 436/518 |
| 6,614,030 B2 | 9/2003 | Maher et al. | 250/458.1 |
| 6,649,908 B2 | 11/2003 | Apffel, Jr. et al. | 250/288 |
| 6,777,670 B1 * | 8/2004 | Farnsworth | 250/285 |
| 6,827,095 B2 * | 12/2004 | O'Connor et al. | 137/15.01 |
| 6,841,774 B1 * | 1/2005 | Weiss | 250/288 |
| 2002/0027197 A1 | 3/2002 | Duholke et al. | 250/288 |
| 2002/0036018 A1 | 3/2002 | McNeely et al. | 137/806 |
| 2002/0041827 A1 | 4/2002 | Yager et al. | 422/57 |
| 2002/0068366 A1 * | 6/2002 | LaDine et al. | 436/518 |
| 2002/0158022 A1 | 10/2002 | Huang et al. | 210/656 |
| 2002/0189947 A1 | 12/2002 | Paul et al. | 204/461 |
| 2002/0199094 A1 | 12/2002 | Strand et al. | 713/150 |
| 2003/0089663 A1 | 5/2003 | Petro et al. | 210/656 |
| 2003/0089846 A1 | 5/2003 | Cooks et al. | 250/281 |
| 2003/0162304 A1 | 8/2003 | Dority et al. | 436/180 |
| 2003/0200794 A1 | 10/2003 | Paul | 73/54.05 |

FOREIGN PATENT DOCUMENTS

| | | |
|---|---|---|
| WO | WO 98/09315 | 3/1998 |
| WO | WO 98/35376 | 8/1998 |
| WO | WO 00/72970 A1 | 12/2000 |
| WO | WO 01/38865 A1 | 5/2001 |
| WO | WO 02/30486 A2 | 4/2002 |

OTHER PUBLICATIONS

Figeys, Daniel et al., *Lab-on-a-Chip: A Revolution in Biological and Medical Sciences*, "Analytical Chemistry," May, 1, 2000.

Wachs, Timothy et al., *Electrospray Device for Coupling Microscale Separations and Other Miniaturized Devices with Electrospray Mass Spectrometry*, "Analytical Chemistry," vol.73, No. 3, Feb. 1, 2001, pp. 632-638.

Morrison, Denise et al., *An Evaluation of a Four-Channel Multiplexed Electrospray Tandem Mass Spectrometry for Higher Throughput Quantitative Analysis*, "Analytical Chemistry," vol. 74, No.8, Apr. 15, 2002, pp. 1896-1902.

Figeys, Daniel et al., *An Integrated Microfluidies-Tandem Mass Spectrometry System for Automated Protein Analysis*, "Analytical Chemistry," vol. 70, No. 18, Sep. 15, 1998, pp. 3728-3724.

Xue, Qifeng et al., *Multichannel Microchip Electrospray Mass Spectrometry*, "Analytical Chemistry," vol.69, No.3, Feb. 1, 1997, pp. 426-430.

Wagner, Knut et al., *An Automated On-Line Multidimensional HPLC System for Protein and Peptide Mapping with Integrated Sample Preparation*, "Analytical Chemistry," vol. 74, No.4, Feb. 15, 2002, pp. 809-820.

Xu, Rongda et al., *Application of Parallel Liquid Chromatography/Mass Spectrometry for High Throughput Microsomal Stability Screening of Compound Libraries*, "Journal of the American Society for Mass Spectrometry," 2002, 13, 155-165.

Van Pelt, Colleen K. et al., *A Four-Column Parallel Chromatography System for Isocratic or Gradient LC/MS Analyses*, "Analytical Chemistry," vol. 73, No. 3, Feb. 1, 2001, pp. 582-588.

Janiszewski, John S. et al., *A High-Capacity LC/MS System for the Bioanalysis of Samples Generated from Plate-Based Metabolic Screening*, "Analytical Chemistry," vol. 73, No. 7, Apr. 1, 2001, pp. 1495-1501.

Zhang, Bailin et al., *High- Throughput Microfabricated CE/ESI-MS: Automated Sampling from a Microwell Plate*, "Analytical Chemistry," vol. 73, No. 11, Jun. 1, 2001, pp. 2675-2681.

Tang, Keqi et al., *Generation of Multiple Electrosprays Using Microfabricated Emitter Arrays for Improved Mass Spectrometric Sensitivity*, "Analytical Chemistry," vol. 73, No. 8, Apr. 15, 2001, pp. 1658-1663.

Liu, Hanghui et al., *Development of Multichannel Devices with an Array of Electrospray Tips for High-Throughput Mass Spectrometry*, "Analytical Chemistry," vol. 72, No. 14, Jul. 15, 2000, pp. 3303-3310.

Yang, Liyu et al., *Evaluation of Four-Channel Multiplexed Electrospray Triple Quadrupole Mass Spectrometer for the Simultaneous Validation of LC/MS/MS Methods in Four Different Preclinical Matrixes*, "Analytical Chemistry," vol. 73, No. 8, Apr. 15, 2001, pp. 1740-1747.

"LCT wit MUX-technology," Internet document from www.micromass.co.uk/systems/sysorg22.asp, Printed Jul. 19, 2002, date of origin unknown.

Xu, Rongda et al., *High-Throughput Mass-Directed Parallel Purification Incorporation a Muliplexed Single Quadrupole Mass Spectrometer*, "Analytical Chemistry," vol. 74, No. 13, Jul. 1, 2002, pp. 3055-3062.

Fang, Liling et al., *High-throughput liquid chromatography ultraviolet/mass spectrometric analysis of combinatorial libraries using an eight-channel multiplexed electrospray time-of-flight mass spectrometer*, "Rapid Communications in Mass Spectrometry," 2002, 16, 1440-1447.

Rohrbacher, Andreas et al., *Muliple-ion-beam time-of-flight mass spectrometer*, Review of Scientific Instruments, vol. 72, No. 8, Aug. 2001,.

Abian, J., *The Coupling of Gas and Liquid Chromatography with Mass Spectrometry*, "Journal of Mass Spectrometry," 34, 157-168, (1999).

"HPLC: Micro LC/MS Analysis of Biological Samples," Web publication; http://www.sge.com, Apr. 1, 1998.

Kameoka, Jun et al., *A Polymeric Microfluidic Chip for CE/MS Determination of Small Molecules*, "Analytical Chemistry," vol. 73, No. 9, May 1, 2001, pp. 1935-1941.

Yin, Hongfeng et al., "A polymeric microfluidic device with integrated mass-spectrometer interface," Web publication, 2002.

Kim, Young Chan et al., "Rapid Sample Cleanup Microchip for Protein Analysis by Electrospray Ionization Mass Spectrometry," *Micro Total Analysis Systems*, J.M. Ramsey and A. van den Berg (eds.), 2001, Kluwer Academic Publishers, the Netherlands, pp. 123-124.

Lazar, Lulia M. et al., "Microchip Integrated Analysis System for Electrospray Mass Spectrometric Analysis of Complex Peptide Mixtures," *Micro Total Analysis Systems*, J.M. Ramsey and A. van den Berg. (eds.), 2001, Kluwer Academic Publishers, the Netherlands, pp. 219-221.

Killeen, Kevin et al., "Chip-MS: A Polymeric Microfluidic Device with Integrated Mass-Spectrometer Interface," *Micro Total Analysis Systems*, J.M. Ramsey and A. van den Berg (eds.), 2001, Kluwer Academic Publishers, the Netherlands, pp. 331-332.

Svedberg, Malin et al., "Electrospray from a Plastic Chip," *Micro Total Analysis Systems*, J.M. Ramsey and A. van den Berg (eds.), 2001, Kluwer Academic Publishers, the Netherlands, pp. 335-336.

Jiang, Yun et al., *Integrated Plastic Microfluidic Devices with ESI-MS for Drug Screening and Residue Analysis*, "Analytical Chemistry," vol. 73, No.9, May 1, 2001, pp. 2048-2053.

Zweigenbaum, Jerry et al., *High-Throughput Bioanalytical LC/MS/MS Determination of Benzodiazepines in Human Urine: 1000 Samples per 12 Hours*, "Analytical Chemistry," vol. 71, No. 13, Jul. 1, 1999, pp. 2294-2300.

Liu H. et al., "A 96-Channel Microdevice for High Throughput Electrospray Ionization Mass Spectrometery (ESI/MS)," Web document published at: http://www.geocities.com/ResearchTriangle/Lab/4688/ht-ms.html, Jun. 9, 1998.

God, Ralf et al., "Using multiparallel HPLC for purification in drug discovery from nature," Web Document published at: http://www.iscpubs.com/articles/aln/n0112god.pdf, Dec. 1, 2001.

Li Jianjun et al., *Integrated system for high-throughput protein identification using a microfabricated device coupled to capillary electrophoresis/nanoelectrospray mass spectrometry*, "Proteomics," 2001, 1, 975-986.

Zhang, B. et al., *Microfabricated Devices for Capillary Electrophoresis-Electrospray Mass Spectrometry*, "Analytical Chemistry," vol. 71, No. 15, Aug. 1, 1999, pp. 3258-3264.

Moore, Roger E. et al., *A Microscale Electrospray Interface Incorporating a Monolithic, Poly(styrenedivinylbenzene) Support for On-Line Liquid Chromatography/Tandem Mass Spectrometry Analysis of Peptides and Proteins*, "Analytical Chemistry," vol. 70, No. 23, Dec. 1, 1998, oo, 4879-4884.

Little, David et al., "A Parallel LC-MS/MS System for High Throughput Quantification in Drug Discovery," Micromass Application Note 248, May 2000.

Dunn, John A. et al., "A Parallel LC/MS/MS System for the High Throughput Quantification of Clinical Trial Samples. A Validation Study," Waters/Micromass Application Note, Oct. 2002.

Tan, Aimin et al., *Chip-Based Solid-Phase Extraction Pretreatment for Direct Electrospray Mass Spectrometry Analysis Using an Array of Monolithic Columns in a Polymeric Substrate*, "Analytical Chemistry," vol. 75, No. 20, Oct. 15, 2003, pp. 5504-5511.

Lin, Yuehe et al., "Microfluidic Devices on Polymer Substrates for Bioanalytical Applications," Web document published at: www. pnl.gov/microcats/aboutus/publication/microchemical/Microtechpresentation.pdf, 1999.

Manz., Andreas et al., *Miniaturization of Separation Techniques Using Planar Chip Technology*, "Journal of High Resolution Chromatography," vol.16, Jul. 1993.

Misharin, Alexander S. et al., *High-Throughput Mass Spectrometer Using Atmospheric Pressure Ionization and a Cylindrical Ion Trap Array*, "Analytical Chemsitry," vol. 77, No. 2, Jan. 15, 2005, pp. 459-470.

* cited by examiner

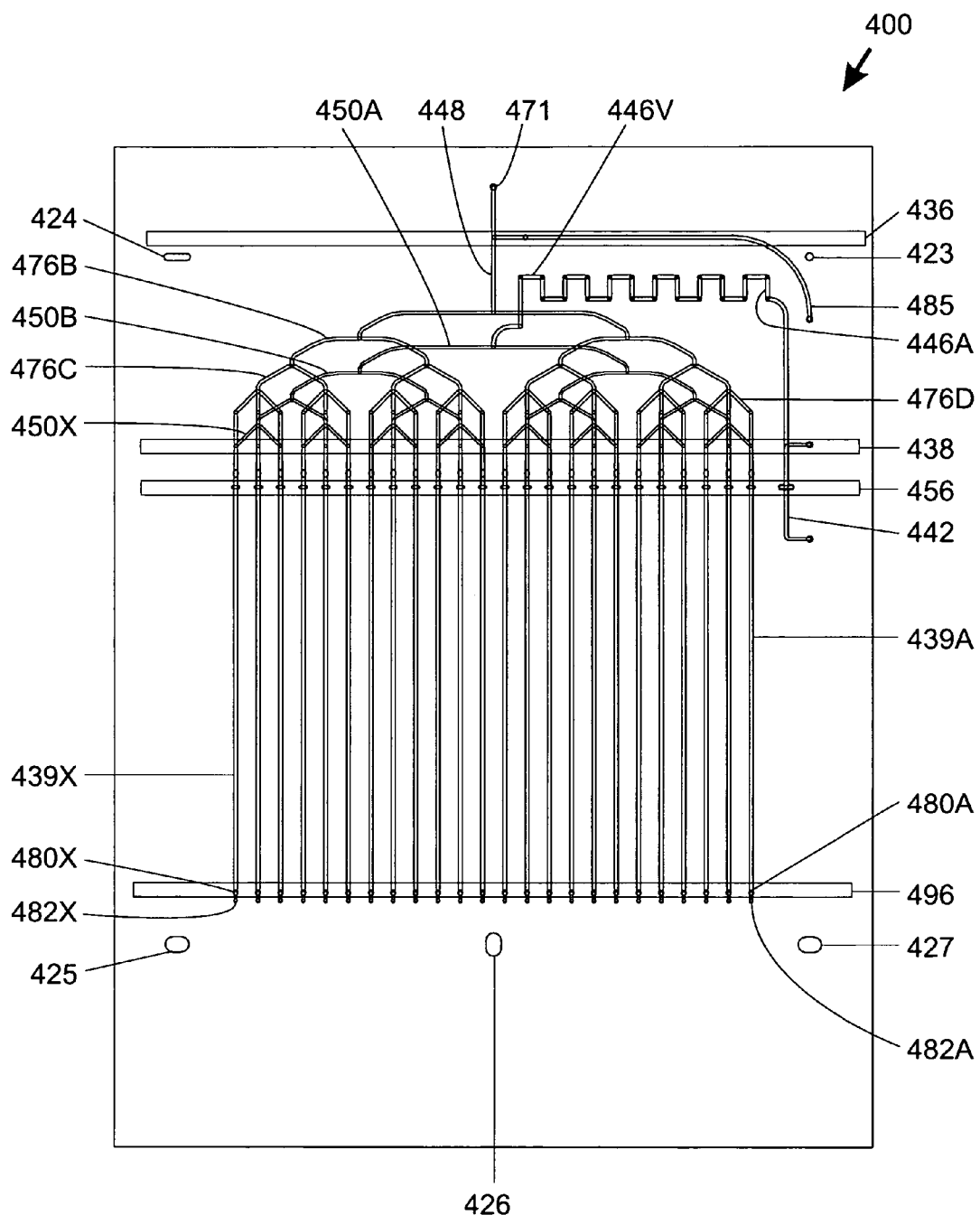
FIG._1

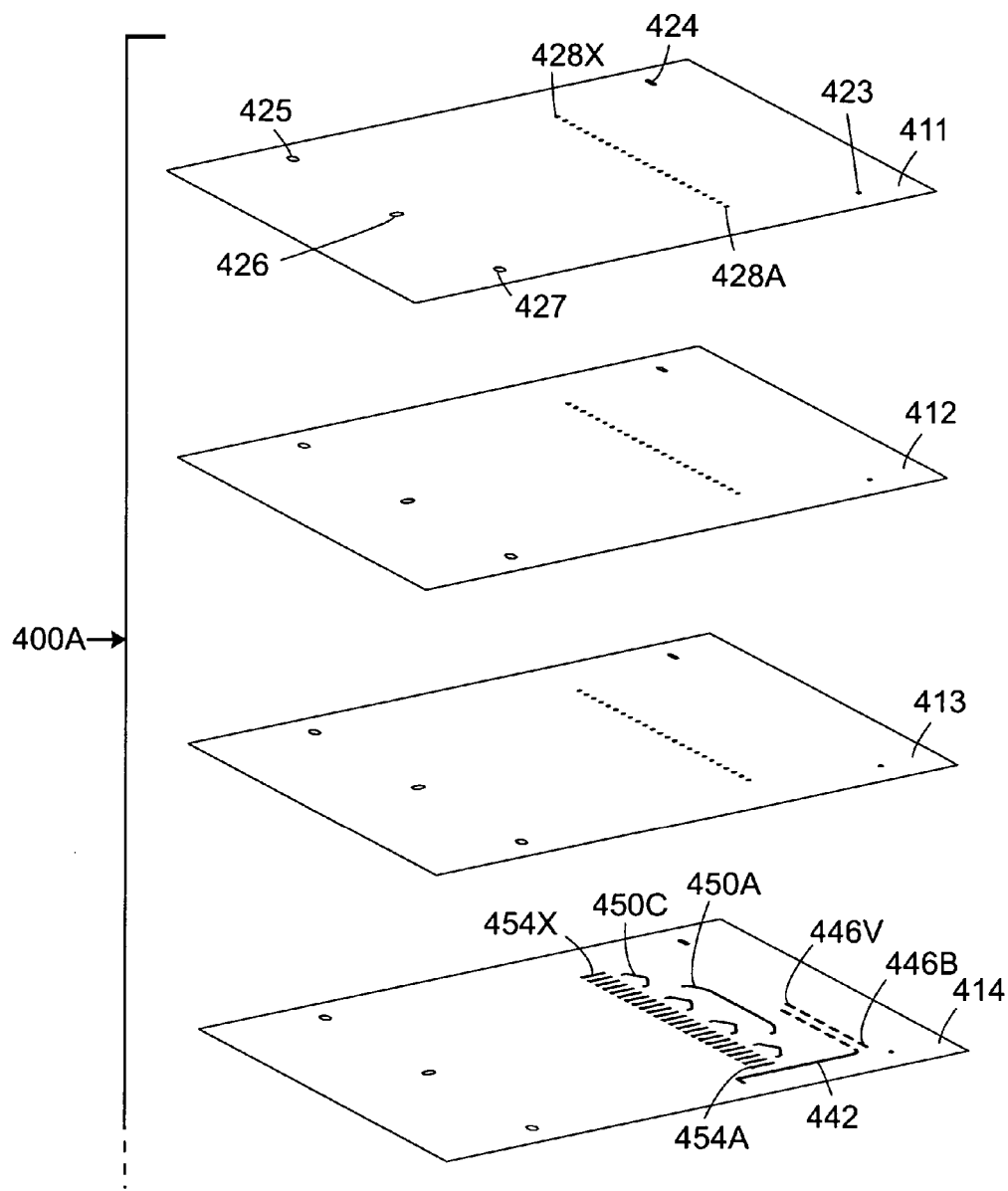
FIG._2A

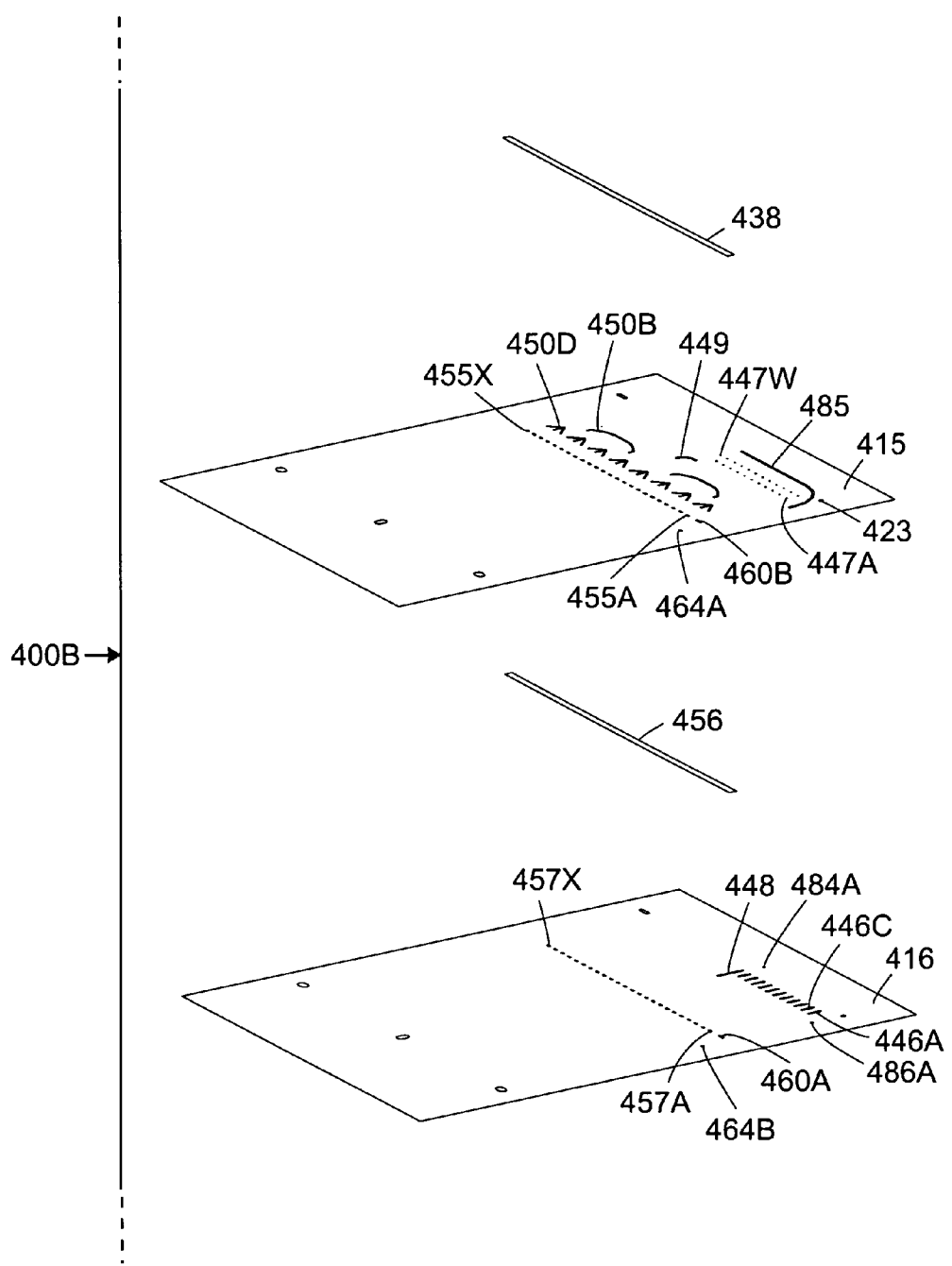
FIG._2B

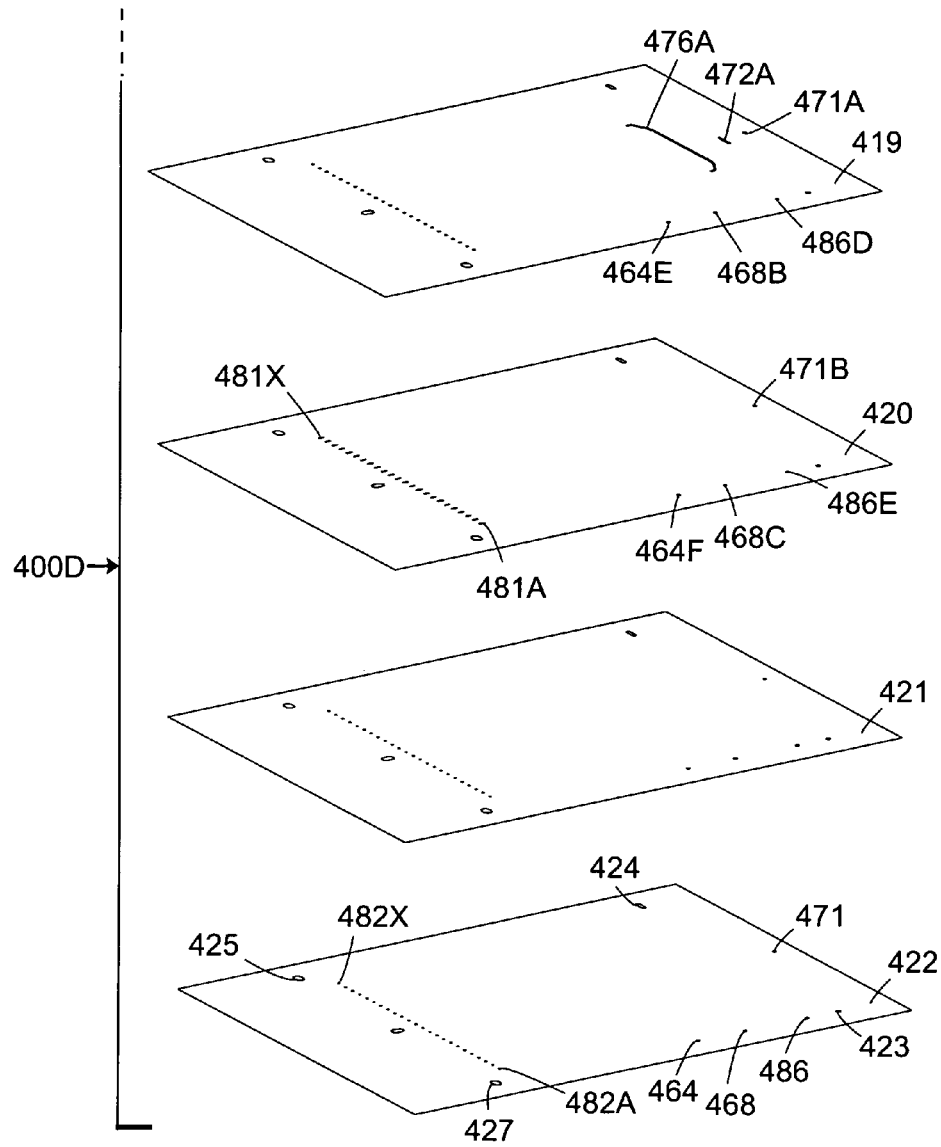
FIG._2D

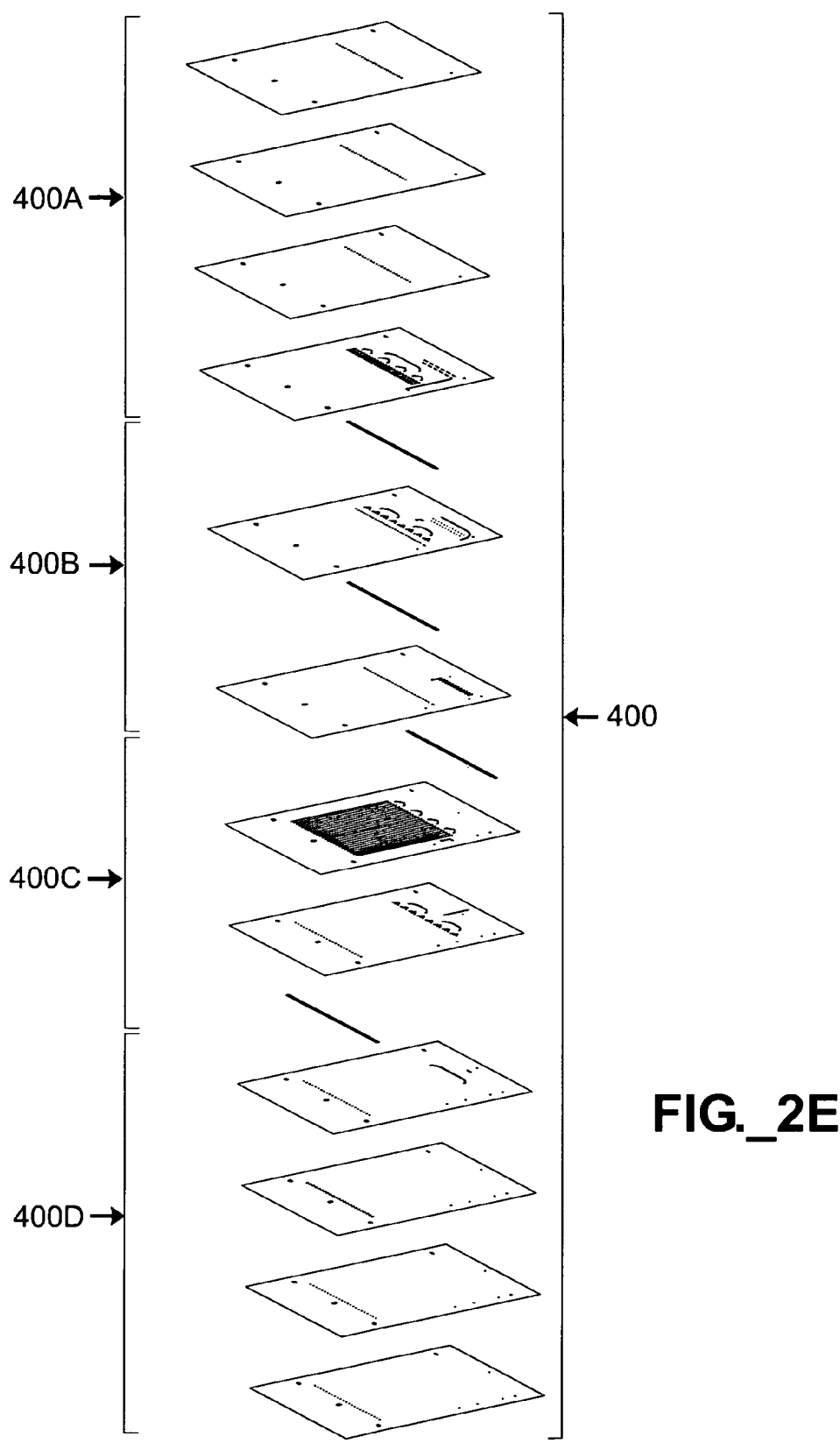
FIG._2E

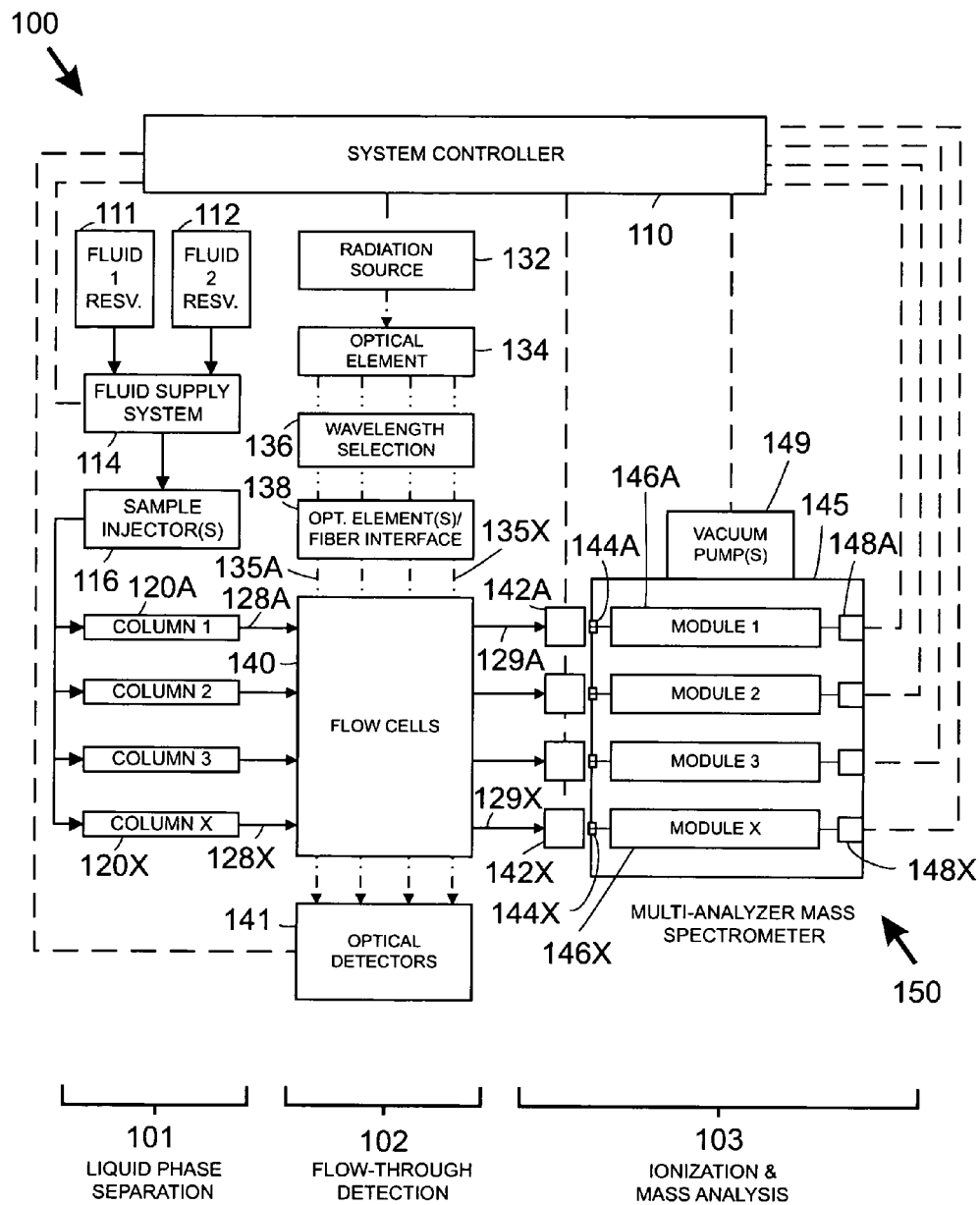
FIG._3

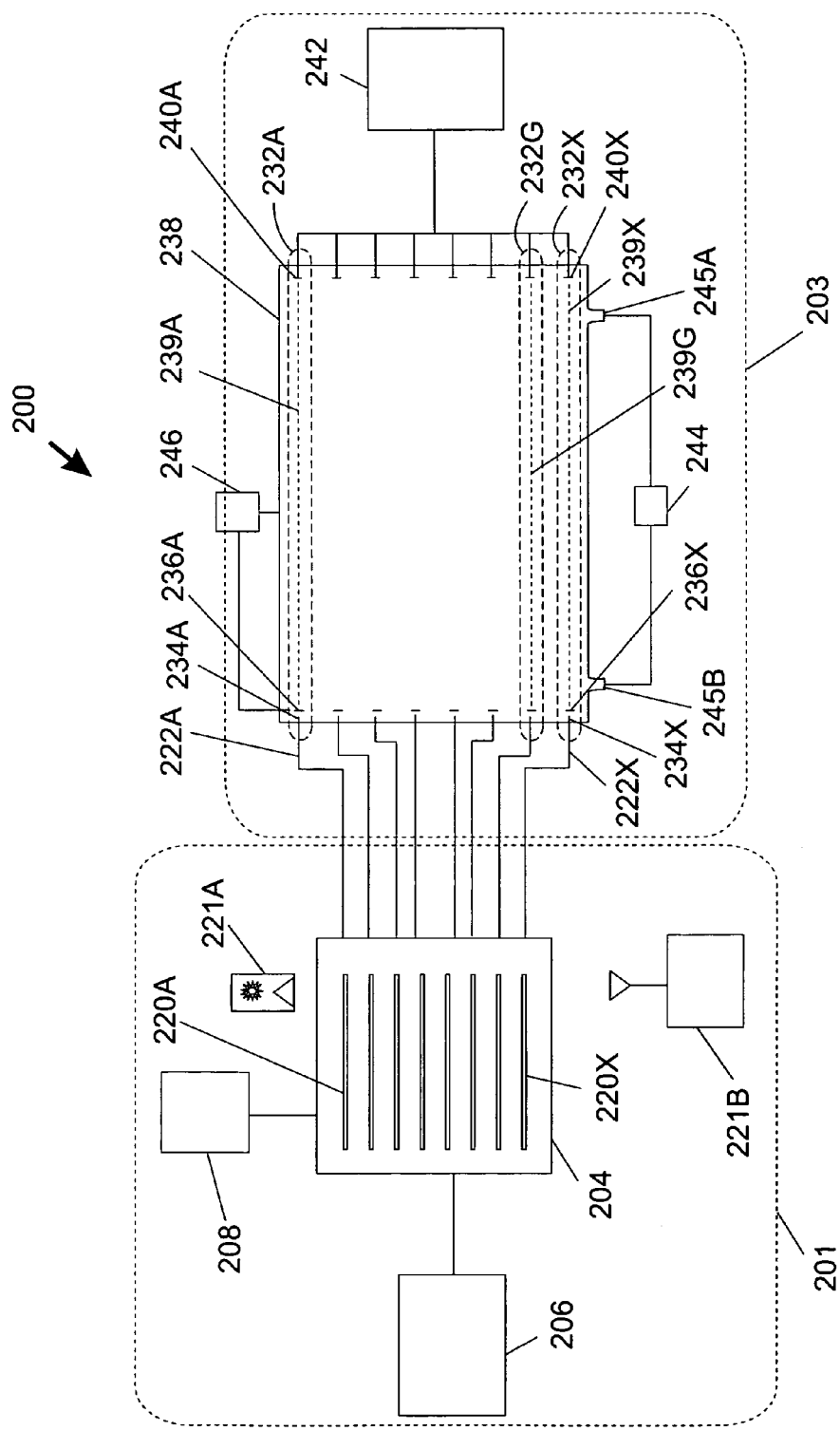
FIG._4

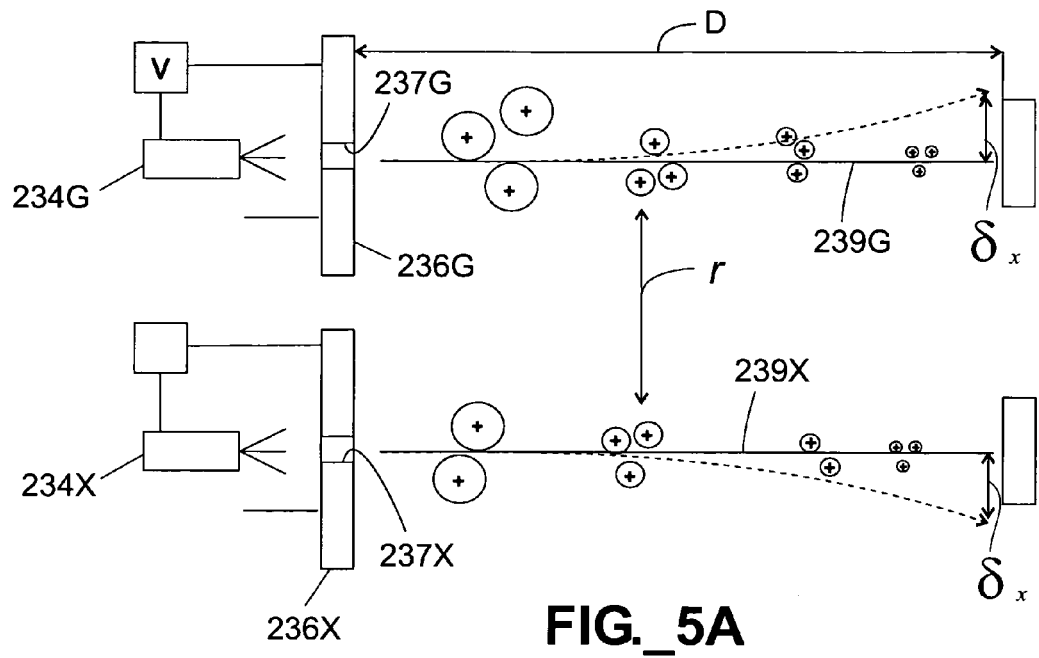
FIG._5A
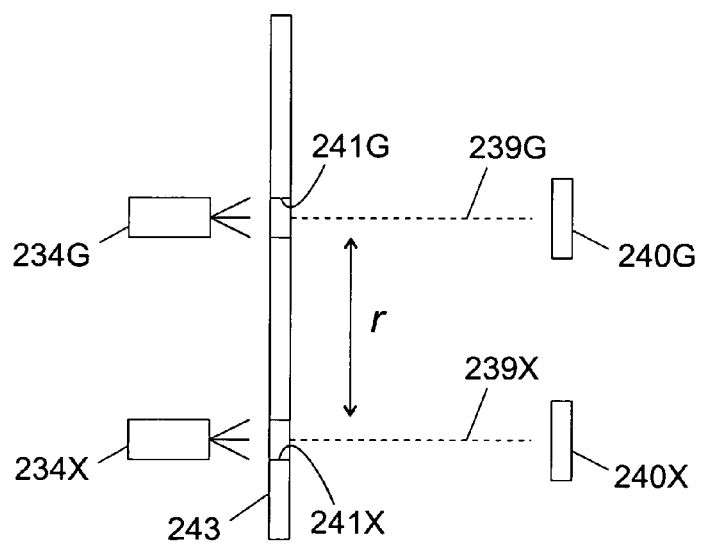
FIG._5B

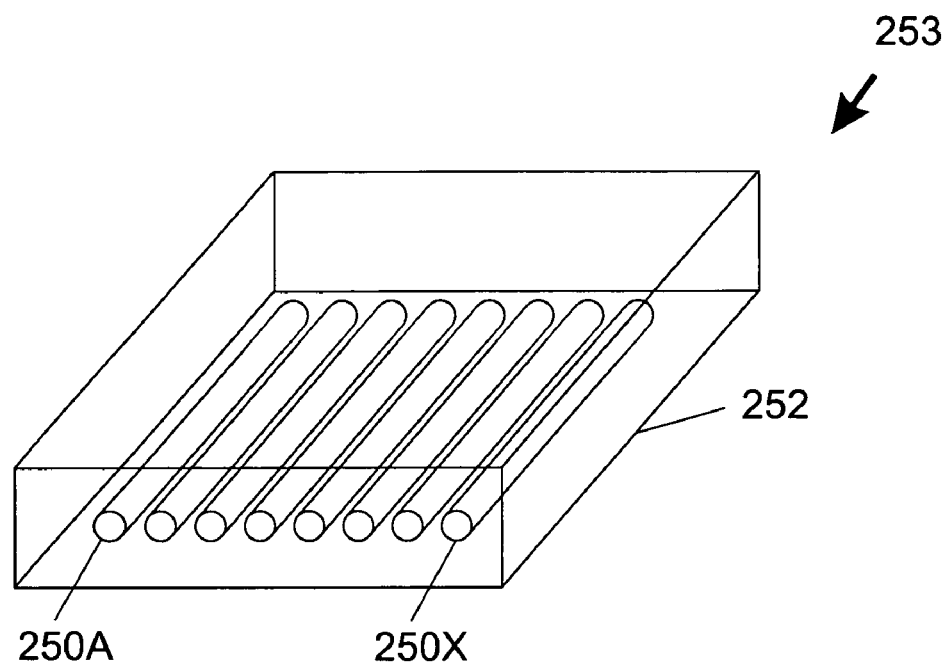
FIG._6

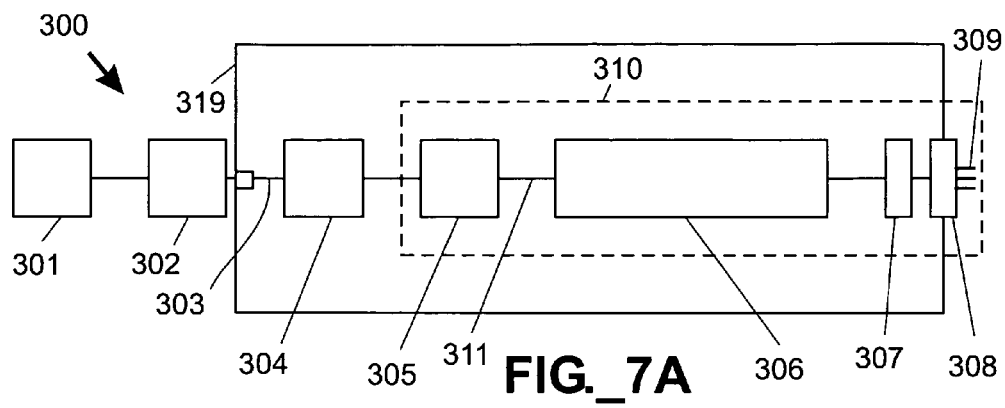
FIG._7A
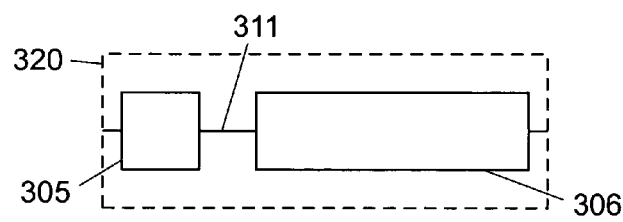
FIG._7B
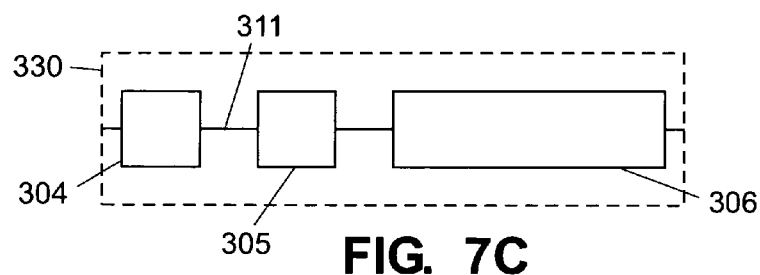
FIG._7C
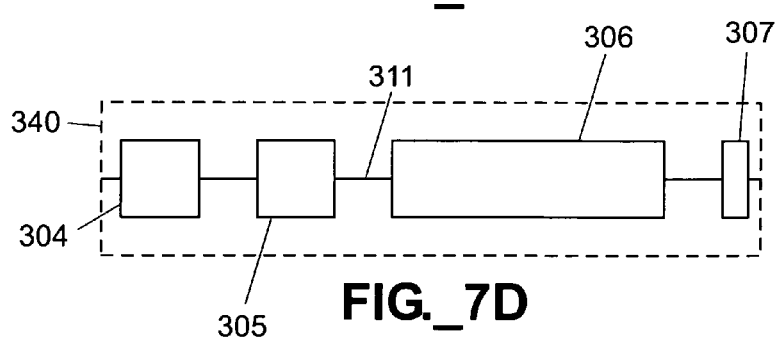
FIG._7D

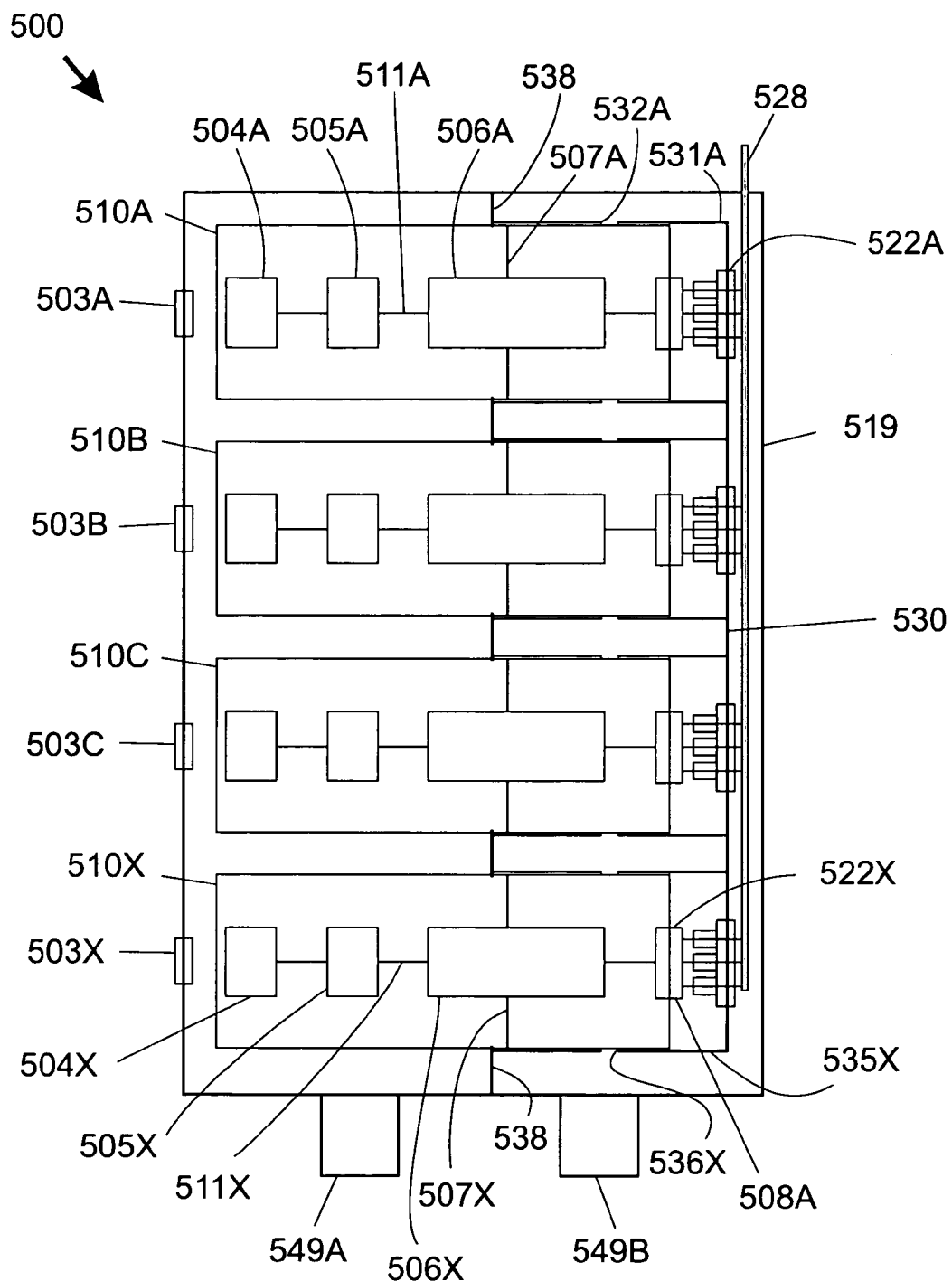
FIG._8B

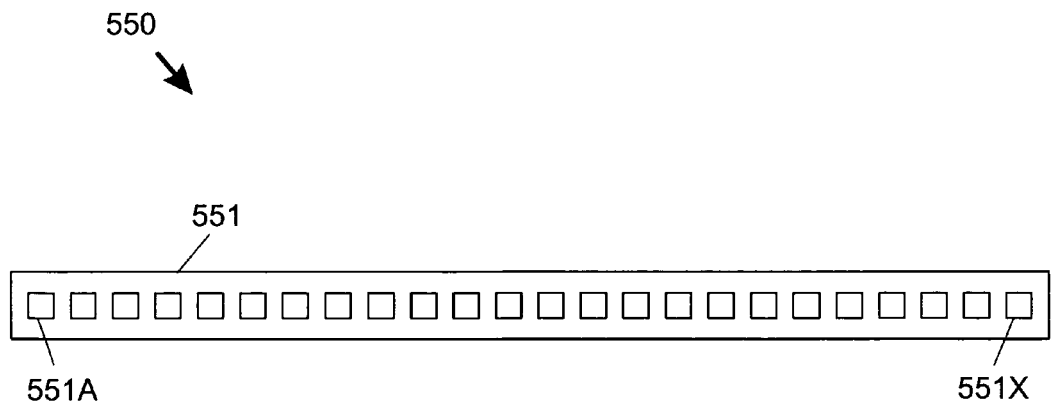
FIG._9A
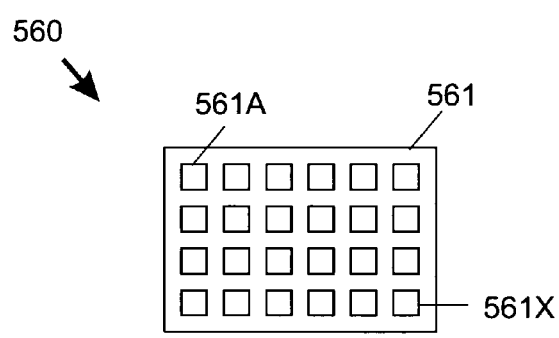
FIG._9B

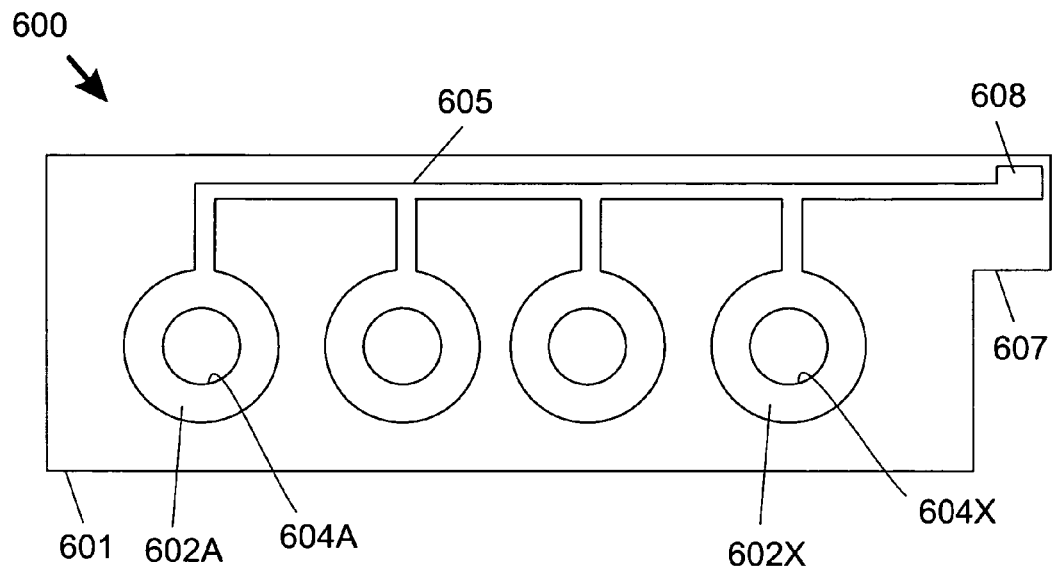
FIG._10
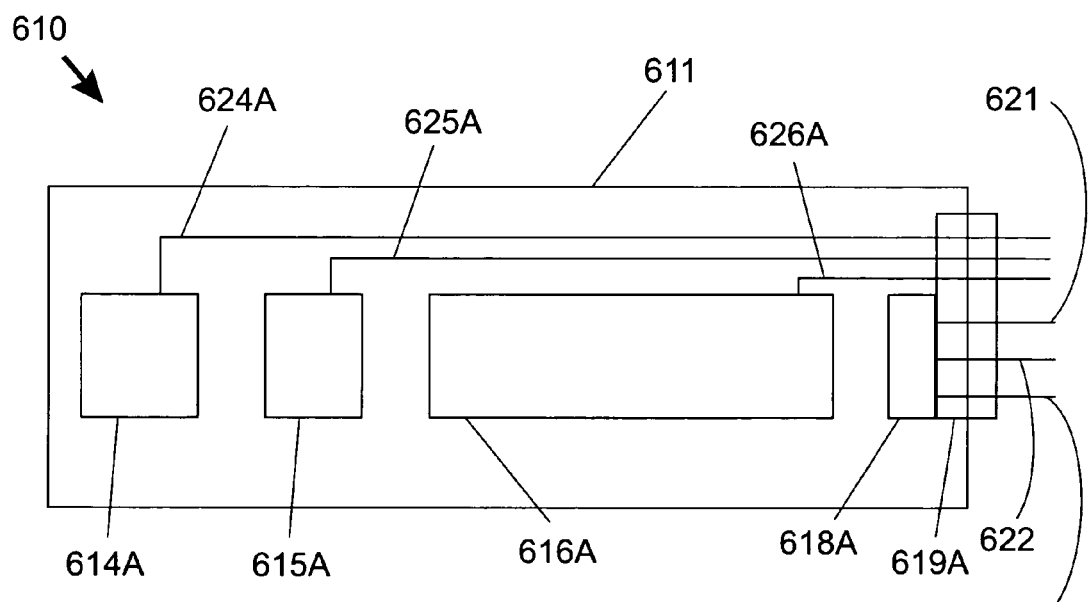
FIG._11

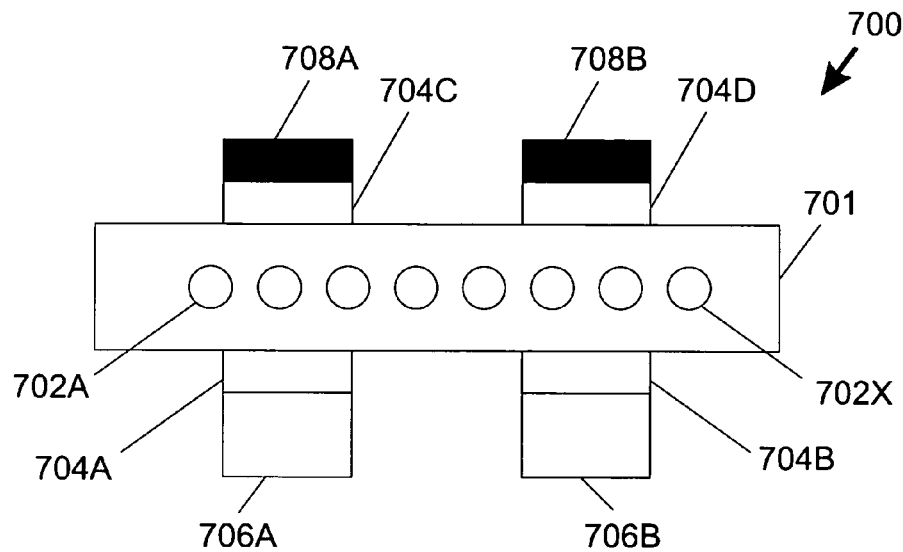
FIG._12A
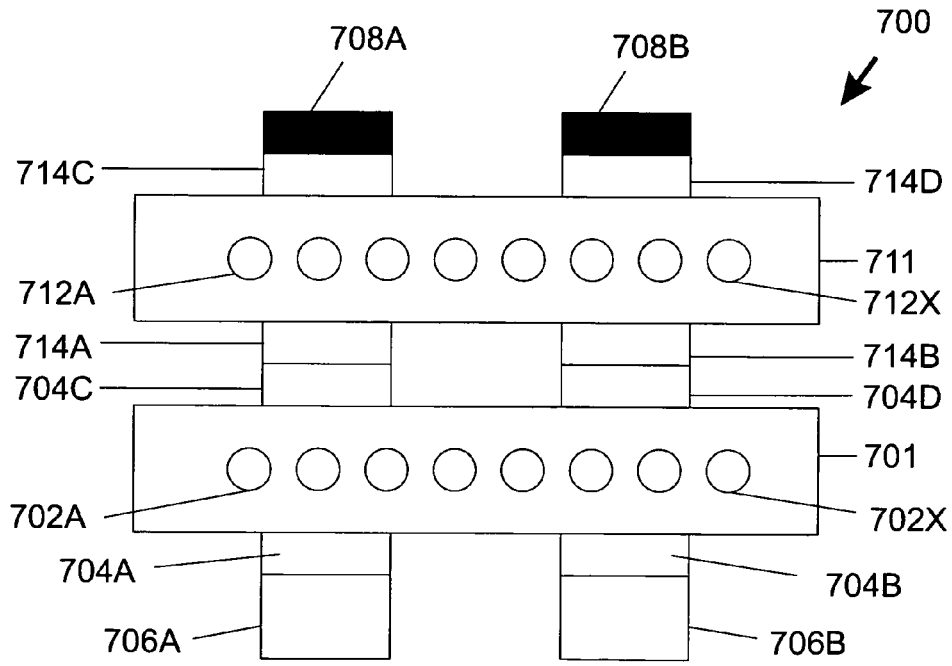
FIG._12B

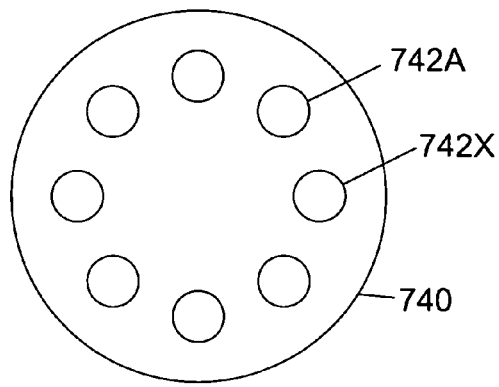
FIG._13
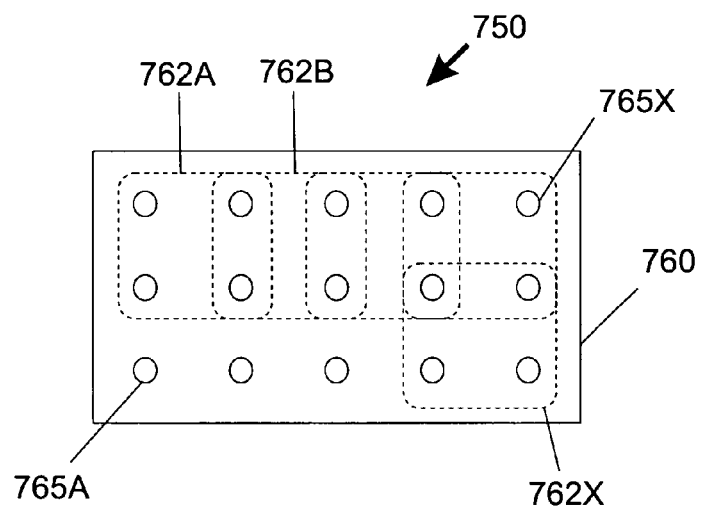
FIG._14A
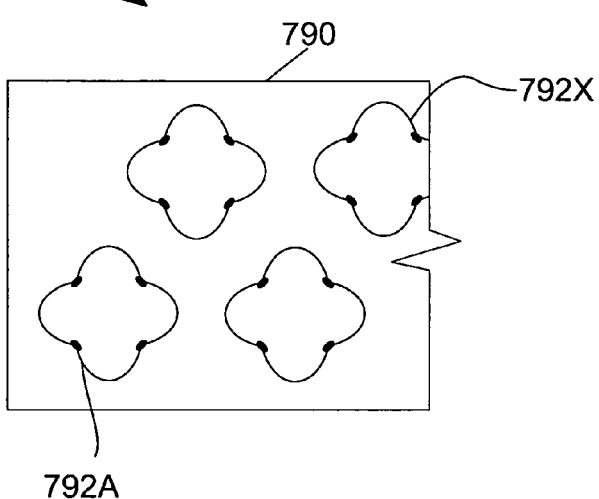
FIG._14B

HIGH THROUGHPUT SYSTEMS AND METHODS FOR PARALLEL SAMPLE ANALYSIS

STATEMENT OF RELATED APPLICATION(S)

This application claims priority to U.S. Provisional Patent Application Ser. No. 60/433,449, filed Dec. 13, 2002.

FIELD OF THE INVENTION

The present invention relates to systems and methods for analyzing multiple samples in parallel using mass spectrometric and/or fluid phase separation techniques.

BACKGROUND OF THE INVENTION

Recent developments in the pharmaceutical industry and in combinatorial chemistry have exponentially increased the number of potentially useful compounds, each of which must be characterized in order to identify their active components and/or establish processes for their synthesis. To more quickly analyze these compounds, researchers have sought to automate analytical processes and to implement analytical processes in parallel.

Various chemical and biochemical fluid phase separation processes are known, including chromatographic, electrophoretic, electrochromatographic, immunoaffinity, gel filtration, and density gradient separation. Each of these processes is capable of separating species in fluid samples with varying degrees of efficiency to promote their analysis.

One particularly useful fluid phase separation process is chromatography, which may be used with a wide variety of sample types and encompasses a number of methods that are used for separating ions or molecules that are dissolved in or otherwise mixed into a solvent. Liquid chromatography "LC") is a physical method of separation wherein a liquid "mobile phase" (typically consisting of one or more solvents) carries a sample containing multiple constituents or species through a separation medium or "stationary phase." Various types of mobile phases and stationary phases may be used. Stationary phase material typically includes a liquid-permeable medium such as packed granules (particulate material) disposed within a tube (or other channel boundary). The packed material contained by the tube or similar boundary is commonly referred to as a "separation column." High pressure is often used to obtain a close-packed column with a minimal void between each particle, since better resolution during use is typically obtained from more tightly packed columns. As an alternative to packed particulate material, a porous monolith or similar matrix may be used. So-called "high performance liquid chromatography" "(HPLC") refers to efficient separation methods that are typically performed at high operating pressures.

Typical interactions between stationary phases and solutes include adsorption, ion-exchange, partitioning, and size exclusion. Examples of types of stationary phases to support such interactions are solids, ionic groups on a resin, liquids on an inert solid support, and porous or semi-porous inert particles, respectively. Commonly employed base materials include silica, alumina, zirconium, or polymeric materials. A stationary phase material may act as a sieve to perform simple size exclusion chromatography, or the stationary phase may include functional groups (e.g., chemical groups) to perform other (e.g., adsorption or ion exchange separation) techniques.

Mobile phase is forced through the stationary phase using means such as, for example, one or more pumps, gravity, voltage-driven electrokinetic flow, or other established means for generating a pressure differential. After sample is injected into the mobile phase, such as with a conventional loop valve, components of the sample will migrate according to interactions with the stationary phase and the flow of such components are retarded to varying degrees. Individual sample components may reside for some time in the stationary phase (where their velocity is essentially zero) until conditions (e.g., a change in solvent concentration) permit a component to emerge from the column with the mobile phase. In other words, as the sample travels through voids or pores in the stationary phase, the sample may be separated into its constituent species due to the attraction of the species to the stationary phase. The time a particular constituent spends in the stationary phase relative to the fraction of time it spends in the mobile phase will determine its velocity through the column. Following separation in an LC column, the eluate stream contains a series of regions having an elevated concentration of individual component species. Thus, HPLC acts to provide relatively pure and discrete samples of each of the components of a compound. Gradient separations using conventional HPLC systems are typically performed within intervals of roughly five to ten minutes, followed by a flush or rinse cycle before another sample is separated in the same separation column.

Following chromatographic separation in a column (or other fluid phase separation), the resulting eluate (or effluent) stream contains a series of regions having elevated concentrations of individual species, which can be detected by various flow-through techniques including spectrophotometric (e.g., UV-Visible absorption), fluorimetric, refractive index, electrochemical, or radioactivity detection. Fluid phase separation with flow-through detection generally provides signal response that is proportional to analyte amount or concentration. As a result, fluid phase separations are often well-suited for quantitative analyses, but less suited for identifying or characterizing individual components-particularly when novel or previously uncharacterized compounds are used.

To provide increased throughput, parallel fluid phase separation systems including multi-column LC separation systems and multi-channel electrophoretic separation systems have been developed.

Another important analytical technique that can complement fluid phase separation is mass spectrometry "MS"), a process that analyzes ions utilizing electromagnetic fields. More specifically, MS permits molecular mass to be measured by determining the mass-to-charge ratio "m/z") of ions generated from target molecules. A system for performing mass spectrometry typically includes an ionization source that generates ions from a sample and delivers them into the gas phase, one or more focusing elements that facilitate ion travel in a specific direction, an analyzer for separating and sorting the ions, and a transducer for sensing the ions as they are sorted and providing an output signal, along with vacuum pumping means and a vacuum enclosure surrounding at least the focusing elements and analyzer. MS is a fast analytical technique that typically provides an output spectrum displaying ion intensity as a function of m/z. One benefit of using MS is that it can provide unique information about the chemical composition of the analyte—information that is much more specific than that can be obtained using flow-through detection technology typically employed with most fluid phase separation processes. The ability to qualitatively identify molecules using MS complements the quantitative capabilities of fluid phase separations, thus providing a second dimension to the analysis.

Various mass spectrometric techniques are known, including time-of-flight ("TOF"), quadrupole, and ion trap. In a TOF analyzer, ions are separated by differences in their velocities as they move in a straight path toward a collector in order of increasing mass-to-charge ratio. In a TOF MS, ions of a like charge are simultaneously emitted from the source with the same initial kinetic energy. Those with a lower mass will have a higher velocity and reach the transducer earlier than ions with a higher mass. In a quadrupole device, a quadrupolar electrical field (comprising radiofrequency and direct-current components) is used to separate ions. An ion trap (e.g., quadrupole-based) can trap ions and separate ions based on their mass-to-charge ratio using a three-dimensional quadrupolar radio frequency electric field. In ion trap instruments, ions of increasing mass-to-charge ratio successively become unstable as the radio frequency voltage is scanned.

Various conventional ionization techniques may be used with mass spectrometry systems. One prevalent technique is electrospray ionization (ESI), which is a "soft" ionization technique. That is, ESI does not rely on extremely high temperatures or extremely high voltages to accomplish ionization, which is advantageous for the analysis of large, complex molecules that tend to decompose under harsh conditions. In ESI, highly charged droplets of analyte dispersed from a capillary in an electric field are evaporated, and the resulting ions are drawn into a MS inlet. Other known ionization techniques include: chemical ionization (which ionizes volatilized molecules by reaction with reagent gas ions); field ionization (which produces ions by subjecting a sample to a strong electric field gradient); spark-source desorption (which uses electrical discharges or sparks to desorb ions from samples); laser desorption (which uses a photon beam to desorb sample molecules); matrix-assisted laser desorption ionization or "MALDI" (which produces ions by laser desorbing sample molecules from a solid or liquid matrix containing a highly UV-absorbing substance); fast atom bombardment or "FAB" (which uses beams of neutral atoms to ionize compounds from the surface of a liquid matrix); and plasma desorption (which uses very high-energy ions to desorb and ionize molecules in solid-film samples).

By coupling the outputs of one or more fluid phase separation process regions to a MS instrument, it becomes possible to both quantify and identify the components of a sample. There exist challenges, however, in providing efficient integrated fluid phase separation/MS systems. MS instruments are typically extremely complex and expensive to operate and maintain, due primarily to the need to precisely control the electromagnetic fields generated within such devices and the need to maintain vacuum conditions therein. Integrated fluid phase separation/MS systems including a single fluid phase process region coupled to a mass spectrometer instrument by way of an ESI interface are known, but they suffer from limited throughput since they can only analyze one sample at a time—and the upstream fluid phase separation process is typically much slower than the downstream mass analysis process. In other words, a fluid phase separation/MS analyzer system having only a single fluid phase separation process region fails to efficiently utilize the rapid analytical capabilities of the MS analyzer portion.

More efficient systems including multiple fluid phase separation process regions coupled to a single MS analyzer are also known and provide higher throughput compared to systems having only a single fluid phase separation process region, but these improved systems still suffer from limited utility. Examples are provided in U.S. Pat. No. 6,410,915 to Bateman, et al.; U.S. Pat. No. 6,191,418 to Hindsgaul, et al.; U.S. Pat. No. 6,066,848 to Kassel, et al.; and U.S. Pat. No. 5,872,010 to Karger, et al., each showing some variation of a multiplexed fluid phase (e.g., LC) separation/MS systems where the outputs of multiple simultaneously-operated fluid phase separation regions are periodically sampled by a single MS device. In these multiplexed systems, however, the MS can sample an effluent stream from only one fluid phase separation process region at a time. While one stream is being analyzed, the others must continue to flow, as these systems have no storage capacity. This inherently results in data loss. To mitigate this data loss, MS sampling must occur very quickly. The MS analyzer thus receives very small plugs of sample-containing effluent, reducing the ability of the MS instrument to integrate data in order to eliminate noise and resulting in reduced signal clarity. Additionally, such conventional systems typically utilize mechanical gating for directing desorbed effluent into a single MS inlet. Mechanical gating components limit the scalability and increase the complexity and cost of the resulting system.

Accordingly, there exists a need for improved analytical systems that permit parallel analysis of multiple samples. Advantageous system characteristics would include scalability to permit a large number of samples to be analyzed simultaneously at a relatively low cost per analysis with a minimal loss of data and/or signal clarity. Ideally, an improved system would be comparatively simple and inexpensive to build, operate, and maintain.

BRIEF DESCRIPTION OF THE DRAWINGS

FIG. 1 is a top view of a twenty-four column microfluidic liquid chromatographic separation device.

FIG. 2A is an exploded perspective view of a first portion, including the first through fourth layers, of the device shown in FIG. 1.

FIG. 2B is an exploded perspective view of a second portion, including the fifth and sixth layers, of the device shown in FIG. 1.

FIG. 2D is an exploded perspective view of a fourth portion, including the ninth through twelfth layers, of the device shown in FIG. 1.

FIG. 2E is a reduced scale composite of FIGS. 2A–2D showing an exploded perspective view of the device of FIG. 1.

FIG. 3 is a schematic showing interconnections between various components of a high throughput analytical system capable of analyzing multiple samples in parallel, the system including a liquid phase separation subsystem, a flow-through detection subsystem, and an ionization and mass analysis subsystem.

FIG. 4 is a simplified diagrammatic view of a high-throughput analytical system including a parallel liquid phase separation apparatus 201 and a multi-channel secondary analysis apparatus.

FIG. 5A is a simplified diagrammatic side view of a portion of the secondary analysis apparatus of FIG. 4 in operation.

FIG. 5B is a simplified diagrammatic side view of a portion of the secondary mass analysis apparatus of FIG. 4 and FIG. 5B.

FIG. 6 is a simplified perspective view of a multi-analyzer mass spectrometer including multiple flight tubes.

FIG. 7A is a simplified diagrammatic side view of an analytical system providing mass analysis utility and including a module.

FIG. 7B is a simplified diagrammatic side view of a first alternative module for use with the system of FIG. 7A.

FIG. 7C is a simplified diagrammatic side view of a second alternative module for use with the system of FIG. 7A.

FIG. 7D is a simplified diagrammatic side view of a third alternative module for use with the system of FIG. 7A.

FIG. 8B is an assembled side cross-sectional view of the mass spectrometer of FIG. 8A.

FIG. 9A is a front diagrammatic view of a mass spectrometer including multiple modules disposed in a one-dimensional array.

FIG. 9B is a front diagrammatic view of a mass spectrometer including multiple modules disposed in a two-dimensional array.

FIG. 10 is a front view of a multi-channel focuser having multiple focusing elements integrated on a common support and having a common edge connector.

FIG. 11 is a simplified diagrammatic side view of a mass analysis module for use with a multi-analyzer modular mass spectrometer.

FIG. 12A is a simplified front cross-sectional view of a mass spectrometer including first mass spectrometer subassembly having multiple mass analysis channels.

FIG. 12B is a simplified front cross-sectional view of a mass spectrometer including first and second mass spectrometer subassemblies each having multiple mass analysis channels.

FIG. 13 is a simplified front cross-sectional schematic view of multiple flight tubes of a multi-channel time-of-flight mass spectrometer.

FIG. 14A is a simplified front cross-sectional schematic view of a first multi-channel quadrupole mass spectrometer.

FIG. 14B is a simplified front cross-sectional schematic view of a second multi-channel quadrupole mass spectrometer.

DETAILED DESCRIPTION OF PREFERRED EMBODIMENTS OF THE INVENTION

Definitions

Figure 2C:
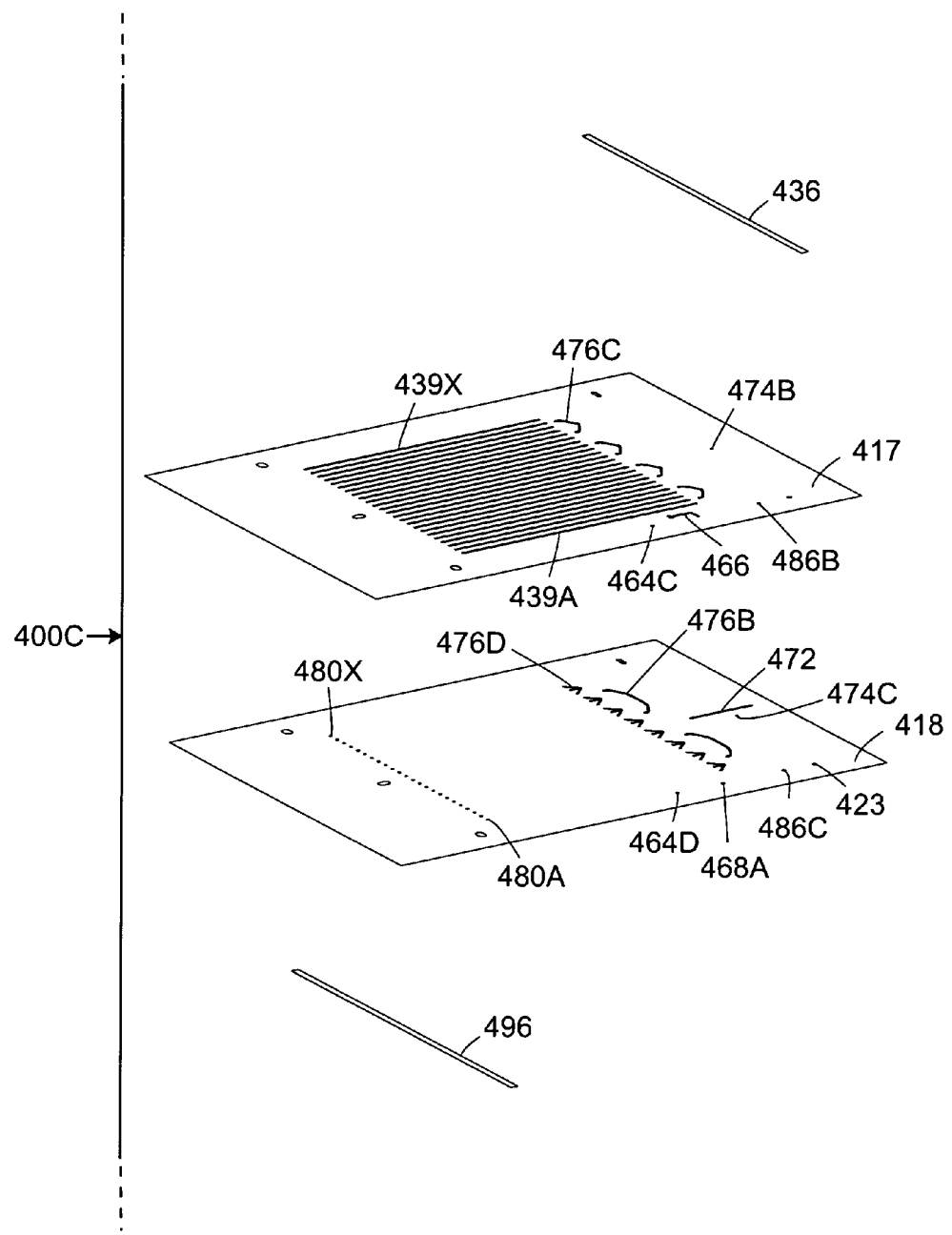
FIG. 2C is an exploded perspective view of a third portion, including the seventh and eighth layers, of the device shown in FIG. 1.

The terms "column" or "separation column" as used herein are used interchangeably and refer to a region of a fluidic device that contains stationary phase material and is adapted to perform a chromatographic separation process.

The term "fluid phase separation process region" refers to any region adapted to perform a fluid (i.e., liquid or gas) phase chemical or biochemical analytical process such as chromatographic, electrophoretic, electrochromatographic, immunoaffinity, gel filtration, and/or density gradient separation.

The term "interpenetrably bound" as used herein refers to the condition of two adjacent polymer surfaces being bound along a substantially indistinct interface resulting from diffusion of polymer chains from each surface into the other.

The term "mass analyzer" as used herein refers to an analytical component that serves to separate ions electromagnetically based on their charge/mass ratio.

The term "microfluidic" as used herein refers to structures or devices through which one or more fluids are capable of being passed or directed and having at least one dimension less than about 500 microns.

The term "parallel" as used herein refers to the ability to concomitantly or substantially concurrently process two or more separate fluid volumes, and does not necessarily refer to a specific channel or chamber structure or layout.

The term "plurality" as used herein refers to a quantity of two or more.

The term "transducer" as used herein refers to a component capable of detecting ions and generating a signal based on such detection.

The term "two-dimensional array" as used herein refers to a grouping of elements having at least two rows and at least two columns.

Fluid Phase Separation Devices

As noted previously, various types of fluid phase separation devices are known, with such devices being capable of separating species in fluid samples utilizing techniques such as chromatographic, electrophoretic, electrochromatographic, immunoaffinity, gel filtration, and/or density gradient separation. Devices including multiple fluid phase separation process regions are also known. Fluid phase separation devices may include both liquid and gas phase separation devices, although liquid phase separation devices are preferred.

Various methods may be used to construct fluid phase separation devices. Simple devices may be fabricated by filling fluidic conduits such as tubes with separation media, with the separation media preferably being retained within the tube using porous screens, filters, or other conventional means.

In preferred embodiments, fluid phase separation devices are microfluidic. Conducting analyses in microfluidic scale offers numerous advantages including reduced sample and reagent usage, reduced waste generation, and improved reaction kinetics. Additionally, microfluidic devices permit a large number of separations to be conducted within a single compact device.

Traditionally, microfluidic devices have been fabricated from rigid materials such as silicon or glass substrates using surface micromachining techniques to define open channels and then affixing a cover to a channel-defining substrate to enclose the channels. There now exist a number of well-established techniques for fabricating microfluidic devices, including machining, micromachining (including, for example, photolithographic wet or dry etching), micromolding, LIGA, soft lithography, embossing, stamping, surface deposition, and/or combinations thereof to define apertures, channels or chambers in one or more surfaces of a material or that penetrate through a material. In addition to silicon and glass, microfluidic devices may now be fabricated from other materials including metals, composites, and polymers.

A preferred method for constructing microfluidic devices utilizes stencil fabrication, involving the lamination of at least three device layers including at least one stencil layer or sheet defining one or more microfluidic channels and/or other microstructures. A stencil layer is preferably substantially planar and has a channel or chamber cut through the entire thickness of the layer to permit substantial fluid movement within that layer. Various means may be used to define such channels or chambers in stencil layers. For example, a computer-controlled plotter modified to accept a cutting blade may be used to cut various patterns through a material layer. Such a blade may be used either to cut sections to be detached and removed from the stencil layer, or to fashion slits that separate regions in the stencil layer without removing any material. Alternatively, a computer-controlled laser cutter may be used to cut detailed patterns through a material layer. Further examples of methods that may be employed to form stencil layers include conventional stamping or die-cutting technologies, including rotary cutters and other high throughput auto-aligning equipment (sometimes referred to as converters). The above-mentioned methods for cutting through a stencil layer or sheet permits robust devices to be fabricated quickly and inexpensively compared to conventional surface micromachining or material deposition techniques that are conventionally employed to produce microfluidic devices.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers mate with one or more adjacent layers (such as stencil layers or substrate layers) to form a substantially enclosed channel-containing device, typically having at least one inlet port and at least one outlet port. The resulting channel(s) typically have substantially rectangular cross-sections.

A wide variety of materials may be used to fabricate microfluidic devices with sandwiched stencil layers, including polymeric, metallic, and/or composite materials, to name a few. Various preferred embodiments utilize porous materials including filtration media. Substrates and stencils may be substantially rigid or flexible. Selection of particular materials for a desired application depends on numerous factors including: the types, concentrations, and residence times of substances (e.g., solvents, reactants, and products) present in regions of a device; temperature; pressure; pH; presence or absence of gases; and optical properties. For instance, particularly desirable polymers include polyolefins, more specifically polypropylenes, and vinyl-based polymers.

Various means may be used to seal or bond layers of a device together. For example, adhesives may be used. In one embodiment, one or more layers of a device may be fabricated from single-or double-sided adhesive tape, although other methods of adhering stencil layers may be used. Portions of the tape (of the desired shape and dimensions) can be cut and removed to form channels, chambers, and/or apertures. A tape stencil can then be placed on a supporting substrate with an appropriate cover layer, between layers of tape, or between layers of other materials. In one embodiment, stencil layers can be stacked on each other. In this embodiment, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thickness of these carrier materials and adhesives may be varied.

Device layers may be directly bonded without using adhesives to provide high bond strength (which is especially desirable for high-pressure applications) and eliminate potential compatibility problems between such adhesives and solvents and/or samples. For example, in one embodiment, multiple layers of 7.5-mil (188 micron) thickness "Clear Tear Seal" polypropylene (American Profol, Cedar Rapids, Iowa) including at least one stencil layer may be stacked together, placed between glass platens and compressed to apply a pressure of 0.26 psi (1.79 kPa) to the layered stack, and then heated in an industrial oven for a period of approximately five hours at a temperature of 154° C. to yield a permanently bonded microstructure well-suited for use with high-pressure column packing methods. In another embodiment, multiple layers of 7.5-mil (188 micron) thickness "Clear Tear Seal" polypropylene (American Profol, Cedar Rapids, Iowa) including at least one stencil layer may be stacked together. Several microfluidic device assemblies may be stacked together, with a thin foil disposed between each device. The stack may then be placed between insulating platens, heated at 152° C. for about 5 hours, cooled with a forced flow of ambient air for at least about 30 minutes, heated again at 146° C. for about 15 hours, and then cooled in a manner identical to the first cooling step. During each heating step, a pressure of about 0.37 psi (2.55 kPa) is applied to the microfluidic devices. Further examples of adhesiveless methods for directly bonding layers of polyolefins including unoriented polypropylene to form stencil-based microfluidic structures are disclosed in commonly assigned U.S. patent application Ser. No. 10/313,231, filed Dec. 6, 2002, which is hereby incorporated by reference as if set forth fully herein.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

In addition to the use of adhesives and the adhesiveless bonding methods discussed above, other techniques may be used to attach one or more of the various layers of microfluidic devices useful with the present invention, as would be recognized by one of ordinary skill in attaching materials. For example, attachment techniques including thermal, chemical, or light-activated bonding steps; mechanical attachment (such as using clamps or screws to apply pressure to the layers); and/or other equivalent coupling methods may be used.

One example of a microfluidic device including multiple fluid phase analytical process regions is provided in FIG. 1 and FIGS. 2A–2E. The device 400 includes twenty-four parallel separation channels 439A–439X containing stationary phase material for performing liquid chromatography. (Although FIG. 1 and FIGS. 2A–2E show the device 400 having twenty-four separation columns 439A–439X, it will be readily apparent to one skilled in the art that any number of columns 439A–439X may be provided. For this reason, the designation "X" is used to represent the last column 439X, with the understanding that "X" represents a variable and could represent any desired number of columns. This convention may be used elsewhere within this document.)

The device 400 is constructed with twelve device layers 411–422, including multiple stencil layers 414–420 and two outer or cover layers 411, 422. Each of the twelve device layers 411–422 defines five alignment holes 423–427, which may be used in conjunction with external pins (not shown) to aid in aligning the layers during construction or in aligning the device 400 with an external interface (not shown) during a packing process or during operation of the device 400. Press-fit interconnects may be provided with either gasketed or gasketless interfaces. Preferably, the device 400 is constructed with materials selected for their compatibility with chemicals typically utilized in performing high performance liquid chromatography, including, water, methanol, ethanol, isopropanol, acetonitrile, ethyl acetate, dimethyl sulfoxide, and mixtures thereof. Specifically, the device materials should be substantially non-absorptive of, and substantially non-degrading when placed into contact with, such chemicals. Suitable device materials include polyolefins such as polypropylene, polyethylene, and copolymers thereof, which have the further benefit of being substantially optically transmissive so as to aid in performing quality control routines (including checking for fabrication defects) and in ascertaining operational information about the device or its contents. For example, each device layer 411–422 may be fabricated from 7.5 mil (188 micron) thickness "Clear Tear Seal" polypropylene (American Profol, Cedar Rapids, Iowa).

Broadly, the device 400 includes various structures adapted to distribute particulate-based slurry material among multiple separation channels 439A–439X (to become separation columns upon addition of stationary phase material), to retain the stationary phase material within the device 400, to mix and distribute mobile phase solvents among the separation channels 439A–439X, to receive samples, to convey eluate streams from the device 400, and to convey a waste stream from the device 400.

The first through third layers 411–413 of the device 400 are identical and define multiple sample ports/vias 428A–428X that permit samples to be supplied to channels 454A–454X defined in the four layer 414. While three separate identical layers 411–413 are shown (to promote strength and increase the aggregate volume of the sample ports/vias 428A–428X to aid in sample loading), a single equivalent layer (not shown) having the same aggregate thickness could be substituted. The fourth through sixth layers 414–416 define a mobile phase distribution network 450 (including elements 450A–450D) adapted to split a supply of mobile phase solvent among twenty-four channel loading segments 454A–454X disposed just upstream of a like number of separation channels (columns) 439A–439X. Upstream of the mobile phase distribution network 450, the fourth through seventh layers 414–417 further define mobile phase channels 448–449 and structures for mixing mobile phase solvents, including a long mixing channel 442, wide slits 460A–460B, alternating channel segments 446A–446V (defined in the fourth and sixth layers 414–416) and vias 447A–447W (defined in the fifth layer 415).

Preferably, the separation channels 439A–439X are adapted to contain stationary phase material such as, for example, silica-based particulate material to which hydrophobic C-18 (or other carbon-based) functional groups have been added. One difficulty associated with prior microfluidic devices has been retaining small particulate matter within separation columns during operation. The present device 400 overcomes this difficulty by the inclusion of a downstream porous frit 496 and a sample loading porous frit 456. Each of the frits 456, 496 (and frits 436, 438) may be fabricated from strips of porous material, e.g., 1-mil thickness Celgard 2500 polypropylene membrane (55% porosity, 0.209×0.054 micron pore size, Celgard Inc., Charlotte, N.C.) and inserted into the appropriate regions of the stacked device layers 411–422 before the layers 411–422 are laminated together. The average pore size of the frit material should be smaller than the average size of the stationary phase particles. Preferably, an adhesiveless bonding method such as one of the methods described previously herein is used to interpenetrably bond the device layers 411–422 (and frits 436, 438, 456, 496) together. Such methods are desirably used to promote high bond strength (e.g., to withstand operation at high internal pressures of preferably at least about 100 psi (690 kPa), more preferably at least about 500 psi (3450 kPa)) and to prevent undesirable interaction between any bonding agent and solvents and/or samples to be supplied to the device 400.

A convenient method for packing stationary phase material within the separation channels 439A–439X is to provide it in the form of a slurry (i.e., particulate material mixed with a solvent such as acetonitrile). Slurry is supplied to the device 400 by way of a slurry inlet port 471 and channel structures defined in the seventh through ninth device layers 417–419. Specifically, the ninth layer 419 defines a slurry via 471A, a waste channel segment 472A, and a large forked channel 476A. The eighth device layer 418 defines two medium forked channels 476B and a slurry channel 472 in fluid communication with the large forked channel 476A defined in the ninth layer 419. The eighth layer 418 further defines eight smaller forked channels 476D each having three outlets, and twenty-four column outlet vias 480A–480X. The seventh layer 417 defines four small forked channels 476C in addition to the separation channels 439A–439X. In the aggregate, the large, medium, small, and smaller forked channels 476A–476D form a slurry distribution network that communicates slurry from a single inlet (e.g., slurry inlet port 471) to twenty-four separation channels 439A–439X (to become separation columns 439A–439X upon addition of stationary phase material). Upon addition of particulate-containing slurry to the separation channels 439A–439X, the particulate stationary phase material is retained within the separation channels by one downstream porous frit 496 and by one sample loading porous frit 456. After stationary phase material is packed into the columns 439A–439X, a sealant (preferably substantially inert such as UV-curable epoxy) may be added to the slurry inlet port 471 to prevent the columns from unpacking during operation of the device 400. The addition of sealant should be controlled to prevent blockage of the waste channel segment 472A.

As an alternative to using packed particulate material, porous monoliths may be used as the stationary phase material. Generally, porous monoliths may be fabricated by flowing a monomer solution into a channel or conduit, and then activating the monomer solution to initiate polymerization. Various formulations and various activation means may be used. The ratio of monomer to solvent in each formulation may be altered to control the degree of porosity of the resulting monolith. A photoinitiator may be added to a monomer solution to permit activation by means of a lamp or other radiation source. If a lamp or other radiation source is used as the initiator, then photomasks may be employed to localize the formation of monoliths to specific areas within a fluidic separation device, particularly if one or more regions of the device body are substantially optically transmissive. Alternatively, chemical initiation or other initiation means may be used. Numerous recipes for preparing monolithic columns suitable for performing chromatographic techniques are known in the art. In one embodiment a monolithic ion-exchange column may be fabricated with a monomer solution of about 2.5 ml of 50 millimolar neutral pH sodium phosphate, 0.18 grams of ammonium sulfate, 44 microliters of diallyl dimethlyammonium chloride, 0.26 grams of methacrylamide, and 0.35 grams of piperazine diacrylamide.

To prepare the device 400 for operation, one or more mobile phase solvents may be supplied to the device 400 through mobile phase inlet ports 464, 468 defined in the twelfth layer 422. These solvents may be optionally pre-mixed upstream of the device 400 using a conventional micromixer. Alternatively, these solvents may be conveyed through several vias (464A–464F, 468A–468C) before mixing. One solvent is provided to the end of the long mixing channel 442, while the other solvent is provided to a short mixing segment 466 that overlaps the mixing channel 442 through wide slits 460A–460B defined in the fifth and sixth layers 415, 416, respectively. One solvent is layered atop the other across the entire width of the long mixing channel 442 to promote diffusive mixing. To ensure that the solvent mixing is complete, however, the combined solvents also flow through an additional mixer composed of alternating channel segments 446A–446V and vias 447A–447W. The net effect of these alternating segments 446A–446V and vias 447A–447W is to cause the combined solvent stream to contract and expand repeatedly, augmenting mixing between the two solvents. The mixed solvents are supplied through channel segments 448, 449 to the distribution network 450 including one large forked channel 450A each having two outlets, two medium forked channels 450B each having two outlets, four small forked channels 450C each having two outlets, and eight smaller forked channels 450D each having three outlets.

Each of the eight smaller forked channels 450A–450D is in fluid communication with three of twenty-four sample loading channels 454A–454X. Additionally, each sample loading channel 454A–454X is in fluid communication with a different sample loading port 428A–428X. Two porous frits 438, 456 are disposed at either end of the sample loading channels 454A–454X. While the first frit 438 technically does not retain any packing material within the device, it may be fabricated from the same material as the second frit 456, which does retain packing material within the columns 439A–439X by way of several vias 457A–457X. To prepare the device 400 for sample loading, solvent flow is temporarily interrupted, an external interface (not shown) previously covering the sample loading ports 428A–428X is opened, and samples are supplied through the sample ports 428A–428X into the sample loading channels 454A–454X. The first and second frits 438, 456 provide a substantial fluidic impedance that prevents fluid flow through the frits 438, 456 at low pressures. This ensures that the samples remain isolated within the sample loading channels 454A–454X during the sample loading procedure. Following sample loading, the sample loading ports 428A–428X are again sealed (e.g., with an external interface) and solvent flow is re-initiated to carry the samples onto the separation columns 439A–439X defined in the seventh layer 417.

While the bulk of the sample and solvent that is supplied to each column 439A–439X travels downstream through the columns 439A–439X, a small split portion of each travels upstream through the columns in the direction of the waste port 485. The split portions of sample and solvent from each column that travel upstream are consolidated into a single waste stream that flows through the slurry distribution network 476, through a portion of the slurry channel 472, then through the short waste segment 472A, vias 474C, 474B, a frit 436, a via 484A, a waste channel 485, vias 486A–486E, and through the waste port 486 to exit the device 400. The purpose of providing both an upstream and downstream path for each sample is to prevent undesirable cross-contamination from one separation run to the next, since this arrangement prevents a portion of a sample from residing in the sample loading channel during a first run and then commingling with another sample during a subsequent run.

Either socratic separation (in which the mobile phase composition remains constant) or, more preferably, gradient separation (in which the mobile phase composition changes with time) may be performed. If multiple separation columns are provided in a single integrated device (such as the device 400) and the makeup of the mobile phase is subject to change over time, then at a common linear distance from the mobile phase inlet it is desirable for mobile phase to have a substantially identical composition from one column to the next. This is achieved with the device 400 due to two factors: (1) volume of the path of each (split) mobile phase solvent substream is substantially the same to each column; and (2) each flow path downstream of the fluidic (mobile phase and sample) inlets is characterized by substantially the same impedance. The first factor, substantially equal substream flow paths, is promoted by design of the mobile phase distribution network 459. The second factor, substantial equality of the impedance of each column, is promoted by both design of the fluidic device 400 (including the slurry distribution network 476) and the fabrication of multiple columns 439A–439X in fluid communication (e.g., having a common outlet) using the slurry packing method disclosed herein. Where multiple columns are in fluid communication with a common outlet, slurry flow within the device is biased toward any low impedance region. The more slurry that flows to a particular region during the packing process, the more particulate is deposited to locally elevate the impedance, thus yielding a self-correcting method for producing substantially equal impedance from one column to the next.

While the embodiment illustrated in FIG. 1 and FIGS. 2A–2E represents a preferred fluidic device, one skilled in the art will recognize that devices according to a wide variety of other designs may be used, whether to perform parallel liquid chromatography or other fluid phase separation processes. For example, other functional structures, such as, but not limited to, sample preparation regions, fraction collectors, splitters, reaction chambers, catalysts, valves, mixers, and/or reservoirs may be provided to permit complex fluid handling and analytical procedures to be executed within a single device and/or system.

Mass Spectrometer Components and Systems

To overcome drawbacks associated with conventional systems including multiple fluid phase separation process regions coupled to a single MS analyzer, preferred embodiments herein utilize a mass spectrometer having multiple inlets, multiple mass analyzers, and multiple transducers to conduct parallel mass analyses of multiple samples. Preferably, the number of mass analyzers equals the number of fluid phase separation process regions to eliminate the need for periodic sampling of different sample streams into the mass spectrometer and thus eliminate the loss of data, the loss of signal clarity, and the need for fluidic switching components. Significant economies can be realized by utilizing common vacuum components and control components, thus reducing the volume and net cost per analyzer of the multi-analyzer mass spectrometer as compared to multiple single-analyzer mass spectrometers.

In one embodiment, a multi-analyzer mass spectrometer is modular, wherein the spectrometer includes a vacuum enclosure, a chassis disposed substantially within the vacuum enclosure, and multiple modules retained by the chassis, with each module including a discrete mass analyzer. Preferably, the chassis includes electrical connectors and each module is adapted to mate with a different connector such that electrical wiring within the spectrometer is greatly simplified. A preferred arrangement for the modules is in a spatially compact two-dimensional array, thus minimizing the footprint of the mass spectrometer and minimizing differences in the requisite path lengths from each fluid separation process region to each corresponding inlet of the multi-analyzer mass spectrometer.

Various multi-analyzer mass spectrometers, associated components, and related analytical systems will be discussed in more detail below.

One example of a high throughput analytical system 100 is provided in FIG. 3. The system 100 includes a liquid phase separation subsystem 101, a flow-through detection subsystem 102, and an ionization and mass analysis subsystem 103. A controller 110 is preferably provided to coordinate operational control of various components of the system. The controller 110 preferably includes microprocessor-based hardware capable of executing a pre-defined or user-defined software instruction set. Data processing and display capability may also be provided by the controller 110 or a separate data processing subsystem (not shown).

The liquid phase separation subsystem 101 may be configured to permit any suitable type of liquid phase separation. In one embodiment, the liquid phase separation subsystem 101 is configured to perform parallel liquid chromatography. The subsystem 101 includes fluid reservoirs 111, 112 (e.g., containing mobile phase solvents such as water, acetonitrile, methanol, DMSO, etc.), a fluid supply system 114 (itself preferably including at least one conventional HPLC pump such as a Shimadzu LC-10AT HPLC pump (Shimadzu Scientific Instruments, Inc., Columbia, Md.) for each fluid reservoir 111, 112), sample injectors 116 such as conventional loop-type sample injection valves or a bank of dispensing needles, and multiple separation columns (or other separation process regions) 120A–120X. (While only four columns 120A–120X are illustrated, it will be readily apparent to one skilled in the art that the system 100 may be scaled to include components to perform virtually any number of simultaneous analyses.) Conventional pre-column injection may be used, or more preferably if the columns are integrated into a microfluidic device such as the device 400 described previously, then direct on-column injection may be used. Capillary conduits (e.g., capillary tubes) 128A–128X are in fluid communication with the columns 120A–120X to convey eluate streams to the flow-through detection subsystem 102. Capillary conduits 128A–128X are particularly preferred over larger-scale tubes if the separation columns 120A–120X are microfluidic to reduce band broadening of the eluate (effluent).

The flow-through detection subsystem 102 may be adapted to perform any suitable type of flow-through detection. Preferred flow-through detection methods include absorbance detection and fluorescence detection. As illustrated, the flow-through detection subsystem 102 includes a radiation source 132, optical elements 134, a wavelength selection element (or, if fluorescence detection is used, interference filter) 136, optional additional optical elements 138 (possibly including a fiber optic interface), flow cells 140, and optical detectors 141. One or more common reference signals may be provided to one or more sensors of the detectors 141. If absorbance (e.g., UV-Visible) detection is used, then the flow cells 140 preferably include an enhanced optical path length through the effluent streams received from the columns 120A–120X. The detectors 141 preferably include multiple sensors disposed in a two-dimensional array. In one example, the detectors 141 are embodied in a multianode photomultiplier tube having sensors disposed in an 8×8 anode array, Hamamatsu model H7546B-03 (Hamamatsu Corp., Bridgewater, N.J.). Further details regarding flow-through detection systems are provided in commonly assigned U.S. patent application Ser. No. 10/699,533 filed Oct. 30, 2003 and No. 60/526,916 filed Dec. 2, 2003, both of which are hereby incorporated by reference.

Following optical detection, the sample-species-containing effluent streams are directed to the ionization and mass analysis subsystem 103, preferably by way of additional capillary conduits 129A–129X. The ionization and mass analysis subsystem 103 includes multiple ionization elements 142A–142X and a multi-analyzer mass spectrometer 150. The spectrometer 150 includes multiple inlets 144A–144X to a vacuum enclosure 145 along with multiple modules 146A–146X and transducers 148A–148X disposed within the enclosure 145. One or more common vacuum pumps 149, preferably disposed in a multi-stage arrangement, serve to evacuate the enclosure 145. Each module 146A–146X preferably includes an ion trap, at least one focusing element, and a mass analyzer. If desired, the transducers 148A–148X may be further integrated into the modules 146A–146X. Preferably, each module 146A–146X and transducer 148A–148X is in electrical communication with the controller 110 by way of a plug or other suitable electrical connector (not shown). One or more common power supplies (not shown) for use with the mass spectrometer 150 may be integrated into the system controller 110 or disposed between the controller 110 and the spectrometer 150.

In operation of the analytical system 100, samples each containing multiple species are provided to the columns 120A–120X by way of the sample injectors 116. The samples are separated into eluate (or effluent) streams each containing a series of elevated concentrations of individual species. The eluate streams are supplied to the flow cells 140 of the flow-through detection system 102 to permit suitable (e.g., optical such as absorbance and/or fluorescence) detection of the species therein. After flowing through the flow cells 140, the fluidic effluent streams are supplied to the ionization elements 142A–142X where they are ionized. While any suitable ionization technique may be used, a preferred ionization technique is electrospray ionization. The ions are supplied through the inlets 144A–144X into the mass spectrometer 150. Each ion stream is preferably supplied to a different analyzer module 146A–146X that serves to separate and sort ions based on charge to mass ratio. The ions are finally detected by the transducers 148A–148X, which supply output signals to the controller 110.

Another high throughput analytical system 200 is illustrated in FIG. 4. The system 200 includes a parallel liquid phase separation apparatus 201 and a multi-channel secondary analysis apparatus 203 preferably embodying a multi-analyzer mass spectrometer. The liquid phase separation apparatus 201 may include any suitable instrument for performing multiple parallel liquid phase separations. In one embodiment, the liquid phase separation apparatus 201 is adapted to perform parallel liquid chromatography. Multiple separation columns 220A–220X are preferably integrated into a single separation device 204. Alternatively, multiple discrete separation columns 220A–220X or other suitable liquid phase separation process regions 220A–220X may be substituted for the separation device 204.

Preferably, a common pressurization and control system 206 is used with the separation device 204. The pressurization and control system 206 may include any one or more suitable pumps or pressurization devices to distribute the mobile phase solvent to the columns 220A–220X to perform the separations. Alternatively, fluid movement may be initiated electrokinetically by the application of voltage. Samples to be analyzed are obtained from a sample source 208, which may be a conventional automated system for retrieving samples from a library, from a particular wellplate, or from any other suitable or desirable source. The sample source 208 may be automated or operated manually.

A flow-through detection apparatus 221 (encompassing elements 221A, 221B) may be included to provide a first analysis of each eluate (effluent) stream. For example, on-board optical windows (not shown) may be included in the device 204 to allow optical detection such as absorbance detection, fluorescence detection, or other desirable optical detection techniques. In a preferred embodiment, the flow-through detection apparatus 221 includes a conventional ultraviolet/visible (UV/Vis) optical detector, including a radiation source 221A and detector 221B. Alternatively, effluent from the device 204 may be routed through one or more external flow cells (such as the flow cells 140 described in connection with FIG. 3) for optical or other flow-through detection.

Multiple fluid conduits 222A–222X carry the effluent from each of the separation columns 220A–220X to the multi-channel secondary analysis apparatus 203. The conduits 222A–222X may include capillary tubing connected to the separation device 204 and/or the multi-channel secondary analysis apparatus 203 using low volume connectors, such as those described in co-pending and commonly-assigned U.S. patent application Ser. No. 10/282,392, which is hereby incorporated by reference. In one example, the conduits 222A–222X are 14.2 mils (about 360 microns) polyimide-coated fused silica tubing. The conduits may be made of any suitable material including, but not limited to, aluminum, stainless steel, glasses, polymers (such as poly [ether ether ketone] [PEEK] or polyimide), or combinations thereof.

In a preferred embodiment, the multi-channel secondary analysis apparatus 203 includes a multi-analyzer mass spectrometer 203. Alternatively, the secondary analysis apparatus 203 may include analytical components adapted to perform any other suitable type of secondary detection technique, such as but not limited to: nuclear magnetic resonance (NMR), evaporative light scattering, ion mobility spectrometry, electrochemical detection, capacitive measurement, or conductivity measurement.

The mass spectrometer 203 includes multiple parallel analysis channels 232A–232X—preferably with one channel 232A–232X being associated with each liquid phase separation process region 220A–220X. In an alternative embodiment (not shown), one mass spectrometry channel 232A–232X may be provided for some number of liquid phase separation process regions (e.g., chromatographic separation columns) 220A–220X and multiplexed. For example, one mass spectrometry channel may be provided for a set of four separation columns with a multiplexing interface. In this manner, if the liquid phase separation apparatus 291 includes twenty-four or ninety-six columns, only six or twenty-four mass spectrometry channels would be required. Of course, the limitations attendant to sampled multiplexed mass spectrometric analyses would arise. One skilled in the art may select the appropriate combination of liquid phase separation process regions, mass spectrometry channels, and interfaces therebetween to accommodate the desired and/or acceptable degree of precision and system complexity.

In a preferred embodiment, each mass spectrometry analysis channel 232A–232X includes a time-of-flight (TOF) mass analyzer. In a preferred embodiment, a single vacuum enclosure 238 surrounds all of the channels 232A–232X. A multi-stage vacuum system 244 is provided to evacuate the vacuum enclosure 238 to the desirable level of vacuum.

Each channel 232A–232X includes an ionization element 234A–234X, which may be disposed inside or outside the vacuum enclosure 238. In a preferred embodiment suitable for analyzing complex large, complex molecules, each ionization element 234A–234X preferably includes an electrospray injector. Electrospray is a "soft" ionization technique. That is, electrospray does not rely on extremely high temperatures or extremely high voltages (relative to other techniques) to accomplish ionization, which is advantageous for analyzing large, complex molecules that tend to decompose under harsh conditions. Electrospray uses the combination of an applied electric field and compressed gas to generate charged droplets of the sample solution. Applying dry gas in conjunction with a vacuum causes the sample droplets to grow increasingly smaller until desolvated, charged sample molecules are produced.

One or more voltage sources 246 provide an electric potential to focusing elements (or "ion optics") 236A–236X to accelerate the ionized sample molecules along the flight path 239A–239X of each channel 232A–232X. Each focusing element 236A–236X preferably includes one or more charged plates each defining a central aperture through which ions are directed. The voltage source 246 also may provide an electric potential to the enclosure 238 to minimize, neutralize, or eliminate any undesirable electromagnetic fields within the enclosure 238. In addition, the voltage source 246 may provide the desired potential to the ionization elements 234A–234X. Alternatively, independent voltage sources (not shown) may be provided for each function.

Multiple transducers 240A–240X are provided for detecting ions, with one each transducer 240A–240X preferably corresponding to a different analysis channel 239A–239X. The transducers 240A–240X may include photomultiplier tubes or other suitable ion detectors. The transducers 240A–240X communicate with a processor 242 that preferably processes and stores signals received from the transducers 240A–240X. In one embodiment, each transducer 240A–240X may include an individual sensor of a multi-channel detector having multiple discrete detection regions. Of course, various focusing elements, mass analyzers, and transducers are known and understood by those skilled in the art, and any combination thereof may be selected to provide the most desirable operating characteristics for the particular application.

In a preferred embodiment where the secondary analysis apparatus performs TOF mass analysis, high voltage (typically about ten to twenty kilovolts) may be applied the focusing elements 236A–236X to accelerate and "focus" the ions so that the ions form a substantially linear beam along each flight path 239A–239X through the channels 232A–232X to the transducers 240A–240X. In an alternative embodiment utilizing quadrupole analysis (discussed below), the flight path for each ion is selectively altered to determine ion content; however, focusing may still be desirable to assure that each flight path begins at a desirable point within the apparatus 203. Once the ions have passed the focusing elements 236A–236X, the voltage of the enclosure 238 may be held at a potential that allows ions to float freely down a flight path 239A–239X with little or no electrostatic interaction with the enclosure 238, the outside environment, or ions traveling in adjacent channels 232A–232X.

Because external forces are substantially neutralized, ions travel down a flight path 239A–239X at a velocity proportional to the force applied by the focusing elements 236A–236X, and the charge and mass of the ions. Thus, smaller ions pass from the focusing elements 236A–236X to the transducers 240A–240X faster than larger ions. The charge of an ion also affects the duration of its travel from an ionization element 234A–234X to a transducer 240A–240X. A transducer 240A–240X is preferably provided for each ionization element 234A–234X and is controlled by time-resolved electronics included in the processor 242 so that each stream of ions may be analyzed separately.

Also, vacuum is preferably maintained within the enclosure 238 to prevent the ions from colliding with ambient molecules, which would distort their flight paths. Thus, the enclosure 238 is preferably capable of maintaining sufficient vacuum to prevent such undesirable interactions (typically below about $10^{-4}$ Torr). In a preferred embodiment, two or more vacuum ports 245A, 245B are positioned at different points on the enclosure 238 and connected to a multi-stage vacuum pumping apparatus 244. In this manner, initial pumping can occur near the inlet portion of the enclosure 238 where new fluid is being introduced into the enclosure 238. The second (and/or third) stage pumps can be used to lower the vacuum within the enclosure 238 to a level appropriate for detection. Additional pumps (not shown) may be provided as necessary. In a preferred embodiment, the liquid phase separation apparatus 201 is microfluidic to reduce the amount of fluid to be injected into the secondary analysis apparatus 203 by a factor of ten to ten thousand as compared to conventional liquid phase separations such as liquid chromatography utilizing tubular columns, thus enabling the maintenance of vacuum conditions within the enclosure 238 without unduly large and costly vacuum pumping systems.

It is critical that the focusing elements 236A–236X, transducers 240A–240X and the enclosure 238 are positioned and controlled so that the ion beams are independent and free of electrostatic interaction. Any substantial interaction between the ion beams (electrostatic or otherwise), focusing elements 236A–236X and transducers 240A–240X may alter ion flight paths sufficiently to induce error. Additionally, if the flight paths are not carefully controlled, cross-talk between channels 232A–232X of the secondary analysis apparatus 203 may occur.

One way to provide the desired channel isolation is to provide a suitable distance between flight paths 239A–239X and sufficiently precise focusing elements 236A–236X to avoid electrostatic or physical interaction between the ion beams. Referring to FIG. 5A, the electromagnetic interaction of parallel ion beams 239G, 239X, i.e., the force $F_2$ exerted by one beam on the other, will tend to deflect the beams some distance $\delta_x$. Assuming the magnetic interaction between the ion beams is negligible, the deflection of the beams $\delta_x$ is proportional to the distance D the particles travel between the focusing elements 236G, 236X and the transducers 240G, 240X, the voltage V applied at the focusing elements 236G, 236X, the distance between the beams r, and the charge q of the ions in the beams according to the following relationship:

$$\delta_x = \frac{1}{16\pi\varepsilon_0}\frac{D^2 q}{Vr^2}$$

Tables 1 and 2 below show the anticipated beam deflection of beams having charges of 500,000 electrons (e.g., 500,000 ions having a charge of one electron) and 1,000,000 electrons, respectively. The deflections are calculated for a range of travel distances and ion optic voltages.

TABLE 1

| Charge (q) | 500,000 e | 500,000 e | 500,000 e | 500,000 e |
|---|---|---|---|---|
| Distance (D) | 10 cm | 20 cm | 10 cm | 20 cm |
| Ion Optics Voltage (V) | 10 kV | 10 kV | 20 kV | 20 kV |
| Distance between beams (r) | Deflection ($\delta_x$) (cm) | Deflection ($\delta_x$) (cm) | Deflection ($\delta_x$) (cm) | Deflection ($\delta_x$) (cm) |
| 0.01 cm | 1.798 | 7.193 | 0.899 | 3.597 |
| 0.05 cm | 0.072 | 0.29 | 0.036 | 0.14 |
| 0.1 cm | 0.018 | 0.072 | 0.009 | 0.036 |
| 0.5 cm | 0.0007 | 0.003 | 0.0004 | 0.001 |
| 1 cm | 0.0002 | 0.0007 | 0.00009 | 0.0004 |

TABLE 2

| Charge (q) | 1,000,000 e | 1,000,000 e | 1,000,000 e | 1,000,000 e |
|---|---|---|---|---|
| Distance (D) | 10 cm | 20 cm | 10 cm | 20 cm |
| Ion Optics Voltage (V) | 10 kV | 10 kV | 20 kV | 20 kV |
| Distance between beams (r) | Deflection ($\delta_x$) (cm) | Deflection ($\delta_x$) (cm) | Deflection ($\delta_x$) (cm) | Deflection ($\delta_x$) (cm) |
| 0.01 cm | 3.597 | 14.387 | 1.798 | 7.193 |
| 0.05 cm | 0.14 | 0.57 | 0.072 | 0.287 |

TABLE 2-continued

| | | | | |
|---|---|---|---|---|
| 0.1 cm | 0.036 | 0.14 | 0.018 | 0.072 |
| 0.5 cm | 0.001 | 0.006 | 0.0007 | 0.003 |
| 1 cm | 0.0004 | 0.001 | 0.0002 | 0.0007 |

Preferably, the distance $\delta_x$ is less than half the width W of the transducer 240G, 240X associated with the ion beam. In certain embodiments, the transducers 240A–240X can be miniaturized even further with the use of technologies such as micro electro mechanical systems (MEMS) where the minimization of interaction between ion beams will become even more critical.

Physical interaction (i.e., collision between ions in the ion streams due to dispersion at the ionizer) may be minimized by providing sufficiently precise focusing elements 236A–236X to focus ion streams before they have the opportunity to disperse over the distance between adjacent channels 232A–232X. The dimensions of conventional focusing elements 236A–236X are such that the distance between channels 232A–232X, which is dictated by the physical constraints of the focusing elements 236A–236X, is typically larger than the dispersal permitted by such elements 236A–236X. Of course, more advanced or miniaturized focusing elements 236A–236X may allow a higher channel density; however, the precision of the focusing elements 236A–236X may be adjusted accordingly if necessary.

Referring to Table 2, for a 0.1 cm diameter detection region, in order to keep the deflection within about one percent of the total detector area of a transducer, each detector needs to be at least about one centimeter apart. Therefore, in a preferred embodiment, each detector is at least about one centimeter apart from every other detector. In a more preferred embodiment intended to further reduce deflection, each detector is at least about two centimeters apart from every other detector.

For example, as illustrated in FIGS. 5A–5B, ionization elements 234A–234X (for clarity, only two channels, 232G and 232X are shown) are placed in proximity to the focusing elements 236A–236X. A voltage difference is applied between the ionization elements 234A–234X and focusing elements 236A–236X in order to accelerate the ions through apertures 237A–237X defined in the focusing elements 236A–236X and along the flight paths 239A–239X of the mass spectrometry channels 232A–232N. As shown in FIG. 5A, each channel 232A–232X may have a distinct set of focusing elements 236A–236X. As noted above, the distance between the flight paths 239A–239X is set so that no interaction between the ions occurs once they have entered the flight paths 239A–239X. Alternatively, as shown in FIG. 5B, the focusing elements may comprise a single conducting plate 243 having a series of apertures 241A–241X with each orifice 241A–241X serving as a focusing element to focus a different ion beam. Because the plate 243 acts to interconnect the apertures 241A–241X, a single voltage source may control all of the focusing elements 236A–236X simultaneously.

In another embodiment, such as shown in FIG. 6, a secondary analysis device 253 may include a TOF mass spectrometer having a multiple flight tubes 250A–250X with one flight tube 250A–250X for each analysis channel, wherein each tube 250A–250X acts to prevent undesirable interactions between channels. In a preferred embodiment, the flight tubes 250A–250X are cylindrical; however, other cross-sectional shapes including rectangles or squares may be used. Where discrete flight tubes 250A–250X are used, the enclosure 252 does not serve to control the flight paths of ion streams, although the enclosure 252 may be used to isolate the secondary analysis device 253 from undesirable ambient electromagnetic fields. Each flight tube 250A–250X may be independently controlled to maintain an isolated environment for each ion path. The tubes 250A–250X may be "floated" within the enclosure 252 and held in place with a non-conducting material such as (but not limited to) ceramics in order to electrically isolate each flight tube 250A–250X. When independent tubes 250A–250X are used, it may be desirable to provide a mean-free-path for molecules that allows maintenance of a desirable vacuum within each tube 250A–250X and the enclosure 252. For example, the flight tubes 250A–250X may be constructed with a material that allows the passage of gases yet maintains a sufficiently uniform electric field so as to allow the isolation of ion paths. In one embodiment, each flight tube 250A–250X is bounded by a porous metallic material such as a metal mesh to facilitate evacuation of molecules from within the enclosure 252 so as to maintain vacuum conditions therein. In another embodiment, each flight tube 250A–250X may be bounded with a solid conductive material having openings (not shown) distributed along the length of the tube 250A–250X. The openings may be sized so as to permit the electric field within the tube to remain intact while allowing the passage of molecules to be evacuated from the enclosure 252 by one or more vacuum pumps (such as embodied in the vacuum system 244 described in connection with FIG. 4).

In preferred embodiments, portions of a parallel analysis apparatus such as multi-analyzer mass spectrometer can be modularized to simplify manufacturing and facilitate scalability. FIG. 7A illustrates an analytical system 300 providing mass analysis utility. The system 300 includes a liquid phase process region 301 in fluid communication with an ionization element 302. A vacuum enclosure 319 defines a sample inlet 303 adjacent to the ionization element 302. An ion trap 304 is preferably provided to trap and selectively discharge ions. Depending on the particular mass analysis technology used to separate ions within the analyzer 306, it may be useful to supply ions to the analyzer 306 in short "bursts" rather than a continuous stream, thus analysis of a first group of ions while a second group is stored in the trap 304 without being discarded. One or more focusing elements 305 are preferably disposed between the ion trap 304 and the analyzer 306. Various types of analyzers 306 may be used to separate and sort ions based on charge-to-mass ratio. A transducer 307 is disposed downstream of the analyzer 306 to detect ions and provide electrical output signals. Sample molecules travel through the system 300 along a central flow path 311. An interface plug 308 having multiple conductors 309 may be provided to connect with external components such as a power supply and/or controller (not shown), with further electrical conductors (not shown) preferably provided along the inner periphery of the enclosure 319, more preferably within each module, to permit communication with various system components. Alternatively or additionally, one or more interface plugs 308 may be disposed within the vacuum enclosure 319 where convenient or necessary.

As shown by the dashed lines in FIGS. 7A–7D, an analyzer 306 may be grouped with one or more other components to form a module 310, 320, 330, 340. Assembling adjacent components into modules helps ensure that physical alignment between critical components is maintained upon assembly of the entire device 300. Alignment is often especially critical between focusing elements 305 and the analyzer 306. Various combinations of components to form modules are shown in FIGS. 7A–7D. In FIG. 7A, the module 310 includes focusing elements 305, analyzer 306, and transducer 307 along with an interface plug 308. In FIG. 7B, the module 320 includes focusing elements 305 and an analyzer 306. In FIG. 7C, the module 330 includes an ion trap 304, focusing elements 305, and an analyzer 306. In FIG. 7D, the module 340 includes an ion trap 304, focusing elements 305, analyzer 306, and a transducer 307.

Figure 8A:
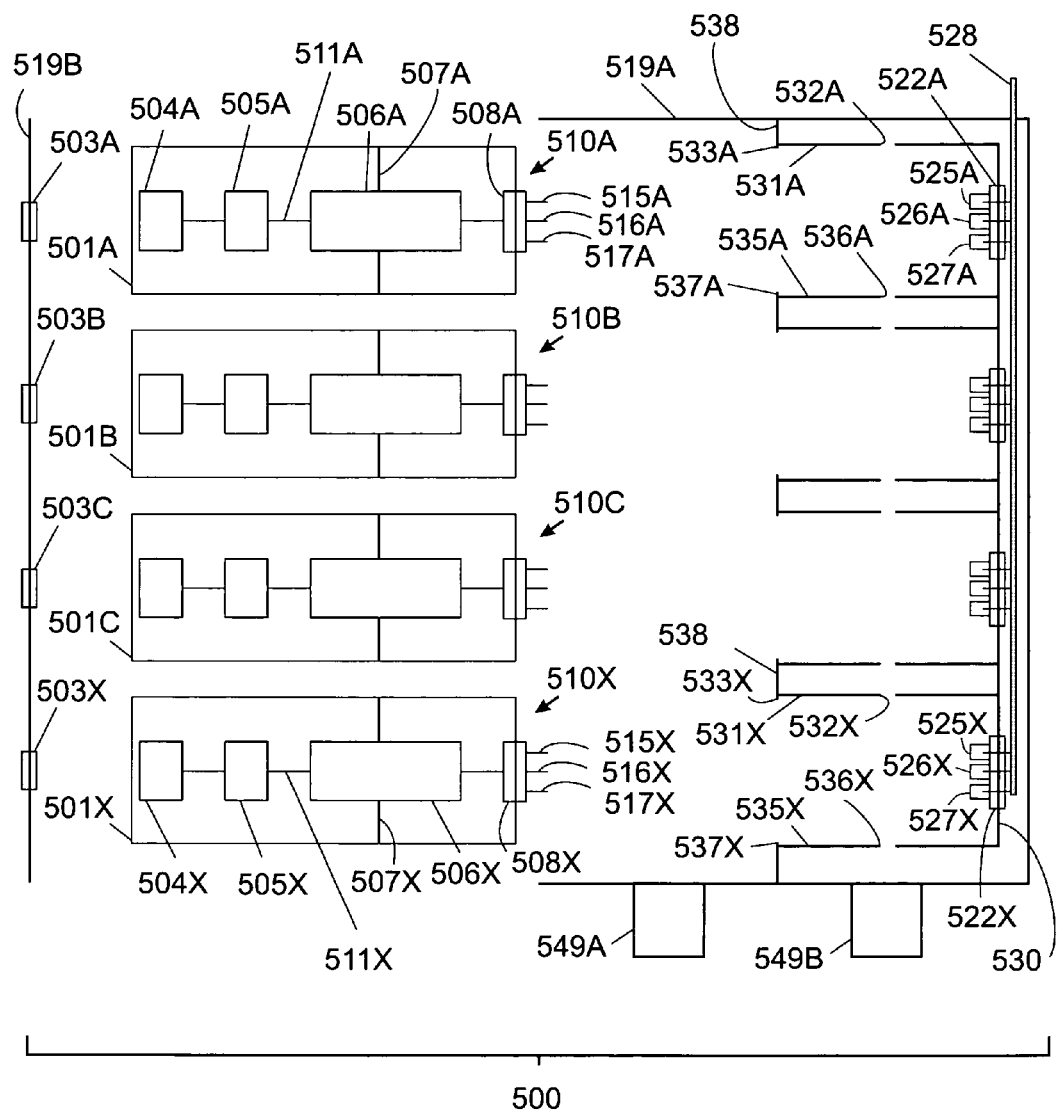
FIG. 8A is an exploded side cross-sectional view of a modular multi-analyzer mass spectrometer including multiple modules, a chassis, and a vacuum enclosure, the spectrometer adapted to permit parallel analysis of multiple samples.

In preferred embodiments, a spectrometer includes multiple modules arranged to permit parallel analysis of multiple samples. One example of a multi-analyzer spectrometer 500 constructed with multiple modules 510A–510X is illustrated in FIGS. 8A–8B. The spectrometer 500 includes a vacuum enclosure 519 constructed in multiple portions 519A, 519B. Preferably, gasketed or equivalent seals (not shown) between the enclosure portions 519A, 519B are provided to prevent leakage of ambient air into the enclosure 519. One enclosure portion 519B defines multiple sample inlets 503A–503X, with one inlet 503A–503X being provided for each module 510A–510X. The other enclosure portion 519A supports an internal chassis 530 adapted to retain multiple modules 510A–510X. Preferably, each module 510A–510X is removably affixed to the chassis 530 to facilitate efficient fabrication of the spectrometer 500 as well as promote easy maintenance and serviceability. For each module 510A–510X, the chassis 530 preferably includes guide members 531A–531X, 535A–535X, seals 533A–533X, 537A–537X, and an interface plug 522A–522X providing connections to multiple conductors 525A–525X, 526A–526X, 527A–527X.

The spectrometer 500 preferably includes multiple vacuum pump stages 549A–549B. While only two vacuum pump stages 549A, 549B are illustrated, more vacuum stages may be provided. Preferably, differential levels of vacuum are maintained within the spectrometer 500, with progressively higher levels of vacuum being maintained along the direction of each ion path 511A–511X. In other words, a lower level of vacuum may be maintained within the enclosure 519 adjacent to the sample inlets 503A–503X than adjacent to the transducers 508A–508X. To facilitate the maintenance of different vacuum states, the enclosure 519 is preferably partitioned into multiple subchambers using internal partitions or baffles 538 disposed substantially perpendicular to the ion paths 511A–511X. As illustrated, partition elements 538 may be disposed between various guide members 531A–531X, 535A–535X. The guide members 531A–531X, 535A–535X preferably define passages 532A–532X, 536A–536X to permit fluid (vacuum) communication with a common vacuum stage 549. Each module 510A–510X preferably includes partitions or baffles 507X—507X corresponding to the partition elements 538, and includes passages or other openings (as described previously) also in communication with the vacuum stage 549. Thus, both the enclosure 519 and modules 510A–510X include appropriate physical baffles or partitions 538, 507A–507X for maintaining differential levels of vacuum within the spectrometer 500 using a minimum number of (e.g., common) vacuum pump stages 549A, 549B. Seals 533A–533X, 537A–537X within the enclosure 519 between the partitions 538 and the modules 510A–510X prevent vacuum leaks and facilitate maintenance of differential vacuum conditions.

The chassis 530, including the guide members 531A–531X, is preferably fabricated with suitably rigid materials to support the modules 510A–510X. In one embodiment, the chassis 530 or at least a portion thereof is fabricated with an electrically insulating material such as non-conductive polymers, ceramics, or composites to promote electrical isolation of the chassis 530 from the modules 510A–510X. Alternatively, if the chassis 530 or at least a portion thereof is constructed with conductive materials, then electrically insulating spacers or standoffs (not shown) may be disposed between the chassis 530 and the modules 510A–510X.

Multiple conductors 525A–525X, 526A–526X, 527A–527X may be grouped into a bundle or electrical bus 528 to minimize the number of physical penetrations through the enclosure 519. In one embodiment, the bus 528 comprises an etched circuit board. Additionally, one or more conductors 525A–525X, 526A–526X, 527A–527X may be common to multiple modules 501A–510X (e.g., ground conductors and/or other conductors if multiple modules 510A–510X are subject to coordinated control through common control inputs) to permit such common conductors to be electrically disposed in series (e.g., "daisy-chained") rather than requiring unnecessarily long parallel conductors for each module 510A–510X.

Each module 510A–510X includes a housing 501A–501X, an ion trap 504A–504X, one or more focusing elements 505A–505X, an analyzer 506A–506X, and a transducer 508A–508X. Each transducer 508A–508X may include an integrally formed plug with multiple conductors 515A–515X, 516A–516X, 517A–517X for mating with corresponding conductors 525A–525X, 526A–526X, 527A–527X in the chassis plugs 522A–522X. Although only three conductors 515A–515X, 516A–1516X, 517A–517X are illustrated for each module 510A–510X, it is to be appreciated that additional conductors may be provided. Additionally, each plug may be distinct from its associated transducer 508A–508X, and each module 510A–510X may include multiple plugs (not shown). Any of the various module components 504A–504X, 505A–505X, 506A–506X, 508A–508X may be aligned with one another within and mounted to their corresponding module housing 501A–501X. Partitions or baffles 507A–507X may be provided within each module 510A–510X, with each module 510A–510X preferably having multiple partitions or baffles disposed along the direction of ion travel 511A–511X through the modules 510A–510X. Each module housing 501A–501X preferably also defines multiple peripheral vacuum openings or passages (not shown) to permit fluid (vacuum) communication between interior portions of the modules 510A–510X and the vacuum pump stages 549A, 549B.

In operation, samples are supplied from external ionization elements (not shown) to the inlers 503A–503X of the spectrometer. Each (sample) ion stream is analyzed in parallel by a different module 510A–510X. Communication between the spectrometer 500 and external control components (not shown) is provided by way of the conductor bundle or bus 528.

In one embodiment, fluid connections between multiple fluid phase separation process regions and a modular multi-analyzer spectrometer are provided with minimal and substantially equal path lengths. To facilitate minimal and substantially equal path lengths, a preferred arrangement for the analyzer modules is in a spatially compact two-dimensional array. Multi-analyzer spectrometers 550, 560 having large numbers of modules disposed in one-dimensional and two-dimensional arrays, respectively, are illustrated in FIGS. 9A–9B. In FIG. 9A, a spectrometer 550 includes twenty-four modules 551A–551X disposed in a single row. Particularly if the spectrometer 550 is interfaced with an external microfluidic fluid phase separation device (such as the device 400 described previously in connection with FIG. 1 and FIGS. 2A–2E) substantially smaller than the spectrometer 550, then to provide equal length fluidic interfaces for each process region and corresponding module 551A–551X many interfaces would be needlessly long. A preferred spectrometer with a more efficient module layout is provided in FIG. 9B. With the modules 561A–561X disposed in a two-dimensional array (e.g., six rows of four columns, although any number of alternative row and column arrangements may be provided) having multiple rows and multiple columns, much shorter equal-length interfaces can be provided between the spectrometer 560 and an upstream fluid phase separation device 400.

As noted previously, components facilitating analysis of different ion streams may be subject to common control. In one embodiment, components used with different spectrometer channels may be integrated. For example, FIG. 10 illustrates a multi-channel focuser 600 having multiple focusing elements 602A–602X integrated on a common support 601. Each focusing element 602A–602X includes a conductive annulus 602A–602X defining a central aperture 604A–604X permitting the passage of ions. A different ion stream may be directed through each different focusing element 602A–602X. Each focusing element 602A–602X may be controlled via one or more common conduits 605. In one embodiment, the conduits 605 terminate at an edge connector 607 having one or more contacts 608. The edge connector 607 may be inserted into an appropriate mating slot connector (not shown) such as may be provided within a surrounding enclosure or chassis. In one embodiment, the support 601 comprises a circuit board, with the conductive annuluses 602A–602X, conduits 605 and contacts 608 being fabricated according to established circuit board fabrication methods.

In certain embodiments, a mass analyzer module includes internal conductors leading to a common connector plug. An example of such a module 610 is provided in FIG. 11. A housing 611 provides structural support for an ion trap 614A, one or more focusing elements 615A, a mass analyzer 616A, and a transducer 618A. A connector plug 619A permits external access to several conductors 621–623, 624A–626A. Certain conductors 624A–626A may be routed substantially within or along housing 611 to transmit signals to or from internal components 614A, 615A, 616A. Routing conductors 624A–626A substantially within or along the housing 611 simplifies the packaging of multiple modules 610 into a large vacuum enclosure (not shown).

In still other embodiments, mass spectrometers may be fabricated with modular sub-assemblies each containing components for multiple analyzer channels such as illustrated in FIGS. 12A–12B. A mass spectrometer 700 includes a first subassembly 701 having multiple analysis channels 702A–702X and vacuum ports 704A–704D. Each channel 702A–702X includes a mass analyzer of any suitable type and desirable related components. A multistage vacuum system 706 including pumps 706A, 706B may be provided in fluid (vacuum) communication with one set of vacuum ports 704A, 704B while another set of vacuum ports 7040, 704D may be sealed with caps 708A, 708B. In the event that it is desired to add additional analysis channels to provide higher throughput, an additional subassembly 711 may be provided, such as illustrated in FIG. 12B. The additional subassembly 711 includes multiple analysis channels 712A–712X and vacuum ports 714A–714D. The two subassemblies 701, 711 are oriented such that vacuum ports 714A, 704B disposed along the bottom of the second subassembly 711 mate with corresponding vacuum ports 7040, 704D disposed along the top of the first subassembly 701 (following removal of the caps 706A, 706B). The caps 706A, 706B are then relocated and positioned to seal the vacuum ports 7140, 714D disposed on top of the second subassembly 711. In this manner, the multi-stage vacuum pumps 706A, 706B may be used to evacuate both the first and second subassemblies 701, 711. Any desirable number of subassemblies 701, 711 may be stacked to provide the desired number of analysis channels. The vacuum system 706 may also be augmented as necessary to maintain desired levels of vacuum within the system 700.

The channels of a particular mass spectrometer may be arranged within a vacuum enclosure or regions thereof in any desirable pattern. For instance, as shown in FIG. 6 and FIGS. 12A–12B, channels may be substantially co-planar. As shown in FIG. 13, mass analysis channels 742A–742X may be arranged in a circular or other pattern within a vacuum enclosure 740. It will be readily apparent to one skilled in the art that any desirable configuration may be provided so long as sufficient inter-channel spacing (and/or shielding) is provided to prevent undesirable interactions between adjacent channels 742A–742X.

In another embodiment illustrated in FIG. 14A, a mass spectrometer 750 includes a vacuum enclosure 760 containing multiple quadrupole mass analyzers 762A–762X, with adjacent analyzers 762A–762X sharing common poles 765A–765X disposed in a matrix. In still another embodiment, shown in FIG. 14B, a mass spectrometer 780 includes multiple glass flight tubes 792A–792X disposed within a vacuum enclosure 790.

High throughput analytical systems according to various embodiments of the present invention provide numerous benefits. For example, continuous output streams from multiple fluid phase separation process regions may be analyzed in parallel by different mass analyzers, thus permitting high throughput operation without the data loss problems typically created by sampling methods. Moreover, because each analyzer of a multi-analyzer mass spectrometer may be disposed within a common vacuum enclosure, fewer vacuum pumps may be required to provide the necessary vacuum conditions. Modular construction provides numerous advantages including more efficient fabrication along with ease of maintenance and servicing. Additionally, control functions and components may be consolidated. The use of common control components not only simplifies fabrication, but also ensures consistent operation from one mass analyzer to the next.

It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention and that the scope of the invention should be interpreted with respect to the following claims.

What is claimed is:

1. A system for analyzing a plurality of samples in parallel, the system comprising:
   a plurality of fluid phase separation process regions;
   a plurality of ionization sources; and
   a mass spectrometer having a plurality of sample inlets and a plurality of transducers; wherein:
   each separation process region is in fluid communication with the mass spectrometer through a different ionization source of the plurality of ionization sources and through a different inlet of the plurality of inlets; and
   each transducer of the plurality of transducers is associated with a different ionization source of the plurality of ionization sources and is associated with a different inlet of the plurality of inlets.

2. A system for analyzing a plurality of samples in parallel, the system comprising:
   a plurality of fluid phase separation process regions;
   a plurality of ionization sources; and
   a mass spectrometer having a plurality of sample inlets, a plurality of mass analyzers, and a plurality of transducers; wherein
   each separation process region is in fluid communication with the mass spectrometer through a different ionization source of the plurality of ionization sources and through a different inlet of the plurality of inlets;
   each ionization source of the plurality of ionization sources supplies ions to a different mass analyzer of the plurality of mass analyzers through a different inlet of the plurality of inlets; and
   each transducer of the plurality of transducers is associated with a different ionization source of the plurality of ionization sources and is associated with a different inlet of the plurality of inlets.

3. The system of claim 2, further comprising a plurality of focusing elements disposed between the plurality of ionization sources and the plurality of mass analyzers.

4. The system of claim 3 wherein:
   the mass spectrometer comprises a chassis and plurality of discrete modules retained by the chassis; and
   each module of the plurality of modules comprises a mass analyzer of the plurality of mass analyzers and at least one of a transducer of the plurality of transducers and a focusing element of the plurality of focusing elements.

5. The system of claim 4 wherein each module of the plurality of modules further includes a selectively dischargeable ion trap disposed between a different inlet of the plurality of inlets and a different mass analyzer of the plurality of mass analyzers.

6. The system of claim 4 wherein each module of the plurality of modules includes a housing defining at least one vacuum passage.

7. The system of claim 4 wherein each module of the plurality of modules is removably affixed to the chassis.

8. The system of claim 4 wherein:
   the chassis includes a plurality of electrical conductors; and
   each module of the plurality of modules is in electrical communication with at least two conductors of the plurality of conductors.

9. The system of claim 8 wherein the chassis includes a plurality of electrical connectors, and each module of the plurality of modules is adapted to mate with a connector of the plurality of connectors.

10. The system of claim 8 wherein the chassis comprises a circuit board.

11. The system of claim 8 wherein the chassis comprises an electrically insulating material.

12. The system of claim 4 wherein the plurality of modules are disposed in a two-dimensional array.

13. The system of claim 1 wherein each inlet of the plurality of inlets is disposed at least about one centimeter apart from every other inlet of the plurality of inlets.

14. The system of claim 4, further comprising at least one vacuum pump, wherein each module of the plurality of modules is in fluid communication with the at least one vacuum pump.

15. The system of claim 4, further comprising a vacuum enclosure and a vacuum pump adapted to evacuate the vacuum enclosure, wherein the plurality of modules are disposed within the vacuum enclosure.

16. The system of claim 15 wherein each module of the plurality of modules comprises at least one internal partition.

17. The system of claim 15 further comprising at least one partition disposed within the vacuum enclosure between at least two modules of the plurality of modules.

18. The system of claim 1 wherein each separation process region of the plurality of separation process regions is microfluidic.

19. The system of claim 18 wherein the plurality of separation process regions are disposed within a unitary microfluidic device.

20. The system of claim 1 wherein the plurality of separation process regions includes a plurality of liquid chromatography columns.

21. The system of claim 2 wherein each mass analyzer of the plurality of mass analyzers comprises any of a time-of-flight mass analyzer, a quadrupole mass analyzer, and an ion trap mass analyzer.

22. The system of claim 2, further comprising a plurality of flow-through detection regions disposed between the plurality of separation process regions and the plurality of mass analyzers.

23. The system of claim 2 wherein the number of separation process regions of the plurality of separation process regions equals the number of mass analyzers of the plurality of mass analyzers.

24. The system of claim 4, further comprising a common controller, wherein each module of the plurality of modules are in electrical communication with the common controller.

25. The system of claim 4, further comprising a common voltage source, wherein each module of the plurality of modules is in electrical communication with the common voltage source.

26. A modular mass spectrometer device for analyzing a plurality of samples in parallel, the device comprising:
   a vacuum enclosure defining a plurality of sample inlets;
   a chassis disposed at least partially within the vacuum enclosure;
   at least one vacuum pump for evacuating the vacuum enclosure; and
   a plurality of modules adapted to mate with the chassis within the vacuum enclosure, the plurality of modules including a plurality of mass analyzers disposed downstream of the plurality of sample inlets and including any of:
      a plurality of focusing elements disposed between the plurality of sample inlets and the plurality of mass analyzers; and
      a plurality of transducers disposed downstream of the plurality of mass analyzers.

27. The device of claim 26 wherein each module of the plurality of modules comprises a mass analyzer of the plurality of mass analyzers, a focusing element of the plurality of focusing elements, and a transducer of the plurality of transducers.

28. The device of claim 26, further comprising a plurality of selectively dischargeable ion traps disposed between the plurality of sample inlets and the plurality of focusing elements.

29. The device of claim 26 wherein each module comprises a housing defining at least one vacuum passage.

30. The device of claim 26 wherein each module of the plurality of modules comprises at least one internal partition.

31. The device of claim 26 further comprising at least one partition disposed within the vacuum enclosure between at least two modules of the plurality of modules.

32. The device of claim 26 wherein:
the chassis includes a plurality of electrical conductors; and
each module of the plurality of modules is in electrical communication with at least two conductors of the plurality of conductors.

33. The device of claim 26 wherein the chassis includes a plurality of electrical connectors, and each module of the plurality of modules is adapted to mate with a connector of the plurality of connectors.

34. The device of claim 26 wherein the chassis comprises an electrically insulating material.

35. The device of claim 26 wherein the chassis comprises a circuit board.

36. The device of claim 26 wherein the plurality of inlets are disposed in a two-dimensional array.

37. The device of claim 26 wherein each inlet of the plurality of inlets is disposed at least about one centimeter apart from every other inlet of the plurality of inlets.

38. The device of claim 26 wherein the plurality of modules are disposed in a two-dimensional array.

39. The device of claim 26 wherein each mass analyzer of the plurality of mass analyzers comprises any of a time-of-flight mass analyzer, a quadrupole mass analyzer, and an ion trap mass analyzer.

40. The device of claim 26, further comprising a plurality of ionization elements.

41. A high throughput analytical system comprising:
a plurality of fluid phase separation process regions; a plurality of ionization elements in fluid communication with the plurality of separation process regions; and
the device of claim 26, wherein each inlet of the plurality of inlets receives ions from a different ionization element of the plurality of ionization elements.

42. The system of claim 41, further comprising a plurality of flow-through detection regions disposed between the plurality of separation process regions and the plurality of inlets.

43. The system of claim 41 wherein the number of separation process regions of the plurality of separation process regions equals the number of modules of the plurality of modules.

44. The system of claim 41 wherein each fluid phase separation process region of the plurality of fluid phase separation process regions is a liquid phase separation process region adapted to perform a liquid phase separation process.

45. The system of claim 1 wherein each fluid phase separation process region of the plurality of fluid phase separation process regions is a liquid phase separation process region adapted to perform a liquid phase separation process.

* * * * *

UNITED STATES PATENT AND TRADEMARK OFFICE
CERTIFICATE OF CORRECTION

PATENT NO. : 6,987,263 B2  Page 1 of 1
APPLICATION NO. : 10/736154
DATED : January 17, 2006
INVENTOR(S) : Steven E. Hobbs et al.

It is certified that error appears in the above-identified patent and that said Letters Patent is hereby corrected as shown below:

In the References Cited, Other Publications, page 2, column 2, "LCT wit MUX-technology" should be -- "LCT with MUX technology" --

In the References Cited, Other Publications, page 3, column 2, "Moore, Roger E. et al., *A Microscale Electrospray Interface Incorporating a Monolithic, Poly (styrenedivinylbenzene) Support for On-Line Liquid Chromatography/Tandem Mass Spectrometry Analysis of Peptides and Proteins*, "Analytical Chemistry," vol. 70, No. 23, Dec. 1, 1998, oo, 4879-4884" should be -- "Moore, Roger E. et al., *A Microscale Electrospray Interface Incorporating a Monolithic, Poly(styrenedivinylbenzene) Support for On-Line Liquid Chromatography/Tandem Mass Spectrometry Analysis of Peptides and Proteins,* "Analytical Chemistry," vol. 70, No. 23, Dec. 1, 1998, pp. 4879-4884" --

Column 2, line 47: "mass spectrometry "MS")" -- mass spectrometry ("MS") --

Column 3, line 4: "time-of-flight "TOF")" should be -- time-of-flight ("TOF") --

Column 12, line 13: "socratic" should be -- isocratic --

Column 22, line 60: "inlers" should be -- inlets --

Signed and Sealed this

Eleventh Day of March, 2008

JON W. DUDAS
*Director of the United States Patent and Trademark Office*